US008152789B2

(12) United States Patent
Starkweather et al.

(10) Patent No.: US 8,152,789 B2
(45) Date of Patent: Apr. 10, 2012

(54) SYSTEM AND METHOD FOR PROVIDING CLOSED LOOP INFUSION FORMULATION DELIVERY

(75) Inventors: Timothy J. Starkweather, Simi Valley, CA (US); Ronald J. Lebel, Sherman Oaks, CA (US); Rajiv Shah, Rancho Palos Verdes, CA (US); Michael E. Miller, Los Angeles, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 2095 days.

(21) Appl. No.: 10/850,637

(22) Filed: May 20, 2004

(65) Prior Publication Data

US 2004/0220517 A1 Nov. 4, 2004

Related U.S. Application Data

(62) Division of application No. 10/033,173, filed on Dec. 26, 2001, now Pat. No. 6,740,072.

(60) Provisional application No. 60/335,664, filed on Oct. 23, 2001.

(51) Int. Cl.
*A61M 31/00* (2006.01)
(52) U.S. Cl. .......................... 604/504; 604/67
(58) Field of Classification Search .............. 604/93.01, 604/67, 66, 131, 113, 500, 503, 504; 600/476, 600/365, 347, 316, 300
See application file for complete search history.

(56) References Cited

U.S. PATENT DOCUMENTS

| | | | |
|---|---|---|---|
| 4,055,175 A | * | 10/1977 | Clemens et al. ............... 604/66 |
| 4,077,405 A | | 3/1978 | Haerten et al. |
| 4,151,845 A | | 5/1979 | Clemens |
| 4,282,872 A | | 8/1981 | Franetzki et al. |
| 4,475,901 A | | 10/1984 | Kraegen et al. |
| 5,101,814 A | | 4/1992 | Palti |
| 5,139,020 A | | 8/1992 | Koestner et al. |

(Continued)

FOREIGN PATENT DOCUMENTS

JP 1-317452 12/1989

(Continued)

OTHER PUBLICATIONS

Notice of Allowance dated Apr. 30, 2009 from related patent U.S. Appl. No. 10/979,980.
Office Action dated Sep. 9, 2008 issued from related Japanese patent application No. 2003-526454.
Decision of Rejection received for JP 2003-526454 dated Mar. 31, 2009.

(Continued)

*Primary Examiner* — Bhisma Mehta
*Assistant Examiner* — Edelmira Bosques
(74) *Attorney, Agent, or Firm* — Foley & Lardner LLP

(57) ABSTRACT

A system and method for providing closed loop infusion formulation delivery which accurately calculates a delivery amount based on a sensed biological state by adjusting an algorithm's programmable control parameters. The algorithm calculates a delivery amount having proportional, derivative, and basal rate components. The control parameters may be adjusted in real time to compensate for changes in a sensed biological state that may result from daily events. Safety limits on the delivery amount may be included in the algorithm. The algorithm may be executed by a computing element within a process controller for controlling closed loop infusion formulation delivery. The biological state is sensed by a sensing device which provides a signal to the controller. The controller calculates an infusion formulation delivery amount based on the signal and sends commands to an infusion formulation delivery device which delivers an amount of infusion formulation determined by the commands.

48 Claims, 17 Drawing Sheets

U.S. PATENT DOCUMENTS

| | | | |
|---|---|---|---|
| 5,190,041 | A | 3/1993 | Palti |
| 5,474,552 | A | 12/1995 | Palti |
| 5,497,772 | A | 3/1996 | Schulman et al. |
| 5,536,249 | A | 7/1996 | Castellano et al. |
| 5,558,640 | A | 9/1996 | Pfeiler et al. |
| 5,569,186 | A | 10/1996 | Lord et al. |
| 5,593,390 | A | 1/1997 | Castellano et al. |
| 5,713,856 | A | 2/1998 | Eggers et al. |
| 5,728,074 | A | 3/1998 | Castellano et al. |
| 5,730,137 | A | 3/1998 | Amano et al. |
| 5,822,715 | A * | 10/1998 | Worthington et al. .......... 702/19 |
| 5,860,919 | A * | 1/1999 | Kiani-Azarbayjany et al. ............................ 600/322 |
| 5,925,021 | A | 7/1999 | Castellano et al. |
| 5,995,860 | A | 11/1999 | Sun et al. |
| 6,049,727 | A | 4/2000 | Crothall |
| 6,221,009 | B1 | 4/2001 | Doi et al. |
| 6,354,299 | B1 | 3/2002 | Fischell et al. |
| 6,453,195 | B1 | 9/2002 | Thompson |
| 6,544,212 | B2 | 4/2003 | Galley et al. |
| 6,551,276 | B1 | 4/2003 | Mann et al. |
| 6,589,229 | B1 | 7/2003 | Connelly et al. |
| 2003/0028089 | A1 * | 2/2003 | Galley et al. ................. 600/365 |

FOREIGN PATENT DOCUMENTS

| | | | |
|---|---|---|---|
| JP | 7-132142 | | 5/1995 |
| JP | 7-148253 | | 6/1995 |
| JP | 9504974 | | 5/1997 |
| JP | 10-504729 | | 5/1998 |
| WO | WO 95/13838 | | 5/1995 |
| WO | WO98/02086 | | 1/1998 |
| WO | WO 00/10628 | * | 3/2000 |
| WO | WO 00/74753 A1 | | 12/2000 |

OTHER PUBLICATIONS

International Search Report received for PCT/US2002/028022 dated Apr. 23, 2003.
International Search Report received for PCT/US2002/28015 dated Jul. 30, 2003.
Non-final Office Action received for U.S. Appl. No. 10/033,173 dated Jul. 10, 2003.
Non-final Office Action received for U.S. Appl. No. 10/033,530 dated May 6, 2004.
Non-final Office Action received for U.S. Appl. No. 10/979,980 dated Dec. 17, 2008.
Notice of Allowance received for U.S. Appl. No. 10/033,530 dated Sep. 21, 2004.
Notice of Allowance received on U.S. Appl. No. 10/033,173 dated Jan. 27, 2004.
Office Action received for CA 2,459,398 dated Nov. 6, 2009.
Supplementary European Search Report for Appln. No. EP 02766221.2 dated Dec. 18, 2008.
Office Action dated Dec. 20, 2010 from related Canadian Patent Application No. 2, 459,398.
Office Action dated Nov. 15, 2010 from related European Patent Application No. 02 766 221.2-2401.
US Notice of Allowance on dated Sep. 22, 2010 from related U.S. Appl. No. 12/490,006.
US Office Action dated Jun. 21, 2010 from related U.S. Appl. No. 12/490,006.
US Office Action dated Jun. 23, 2011 from related U.S. Appl. No. 12/907,454.

* cited by examiner

SYSTEM AND METHOD FOR PROVIDING CLOSED LOOP INFUSION FORMULATION DELIVERY

CROSS-REFERENCE TO RELATED APPLICATIONS

This application is a divisional of and claims priority from U.S. patent application Ser. No. 10/033,173 filed Dec. 26, 2001, which in turn claims the benefit of U.S. Provisional Patent Application No. 60/335,664, filed Oct. 23, 2001, and relates to U.S. Provisional Patent Application No. 60/318,062, filed Sep. 7, 2001 each of which are hereby incorporated by reference herein.

BACKGROUND OF THE INVENTION

1. Field of the Invention

The present invention relates generally, to infusion pump systems for the delivery of infusion formulations, and in particular, to a closed-loop algorithm for use in conjunction with a process controller for controlling the delivery of an infusion formulation to a body based in part on sensed blood glucose levels within the body.

2. Description of Related Art

Infusion pumps have been used for the programmed delivery of measured doses of an infusion formulation. (An infusion formulation is defined in the present disclosure as the substance being delivered by the infusion pump. This substance may comprise either a mixture of different components or it may be a single, pure substance, including, but not limited to drugs, dyes or other indicators, nutrient, or the like.) A typical example of such use is the delivery of an insulin formulation to a patient.

In the case where the infusion formulation is an insulin formulation, a sensing device may regulate the delivery of the insulin formulation by sensing the levels of blood glucose in the person. The delivery of the insulin formulation may be controlled by a control device associated with the pump having as an input a sensed blood glucose level. The control device may control activation of the pump to deliver an appropriate amount of the insulin formulation in accordance with the sensed blood glucose level.

Insulin is a protein hormone normally formed within the human pancreas. Because it regulates carbohydrate (sugar) metabolism, insulin is required for normal metabolic function. More specifically, insulin helps the body metabolize glucose. To avoid medical problems such as hypoglycemia and hyperglycemia, blood glucose levels should be maintained within a specific range. A normal range for glucose in the human body may be between 85 and 120 milligrams/deciliter (mg/dl).

In a non-diabetic person, insulin is secreted by the pancreas in small amounts throughout the day (basal rate of insulin secretion). In addition, the amount of insulin secreted by the pancreas may be modified under certain circumstances. For example, the pancreas of a non-diabetic person normally secretes larger amounts of insulin (bolus rate of insulin secretion) when the person ingests a meal to prevent postprandial hyperglycemia, i.e., abnormally increased sugar content in the blood.

In contrast to the non-diabetic person, a diabetic person's pancreas may not secrete the required amount of insulin. Thus, the diabetic person has to somehow artificially introduce the insulin into the body. One method of introducing the insulin is by the conventional insulin formulation injection method using a syringe. Using this method, the body's blood glucose level may be monitored (for example, by checking a blood sample) and the amount of insulin to be injected may be adjusted accordingly. For example, after a meal the blood glucose level may be monitored and an appropriate amount of insulin may be injected into the bloodstream of the user.

In the alternative, a diabetic person may choose to use an infusion pump such as the infusion pump described above. By using an infusion pump, a diabetic person may be able to adjust insulin delivery rates for the pump in accordance with the user's needs. These needs may be determined based on prior experience and/or the results of glucose monitoring (for example, by a sensing device in combination with a communication device).

In addition, infusion pumps may be engineered to function as an artificial pancreas. Such an infusion pump may deliver a specific amount of insulin formulation at specific intervals. As discussed above, a sensing device associated with the pump may monitor the blood glucose level of the user and the blood glucose level may then be used by the pump to automatically regulate the delivery of the insulin formulation.

It is known to use as a control device a process controller for performing automatic regulation of the infusion pump. The process controller, for example a processor or other computing element, controls the process such that a process variable is maintained at a desired set point value (also referred to in the present disclosure as the "goal"). Such process controllers typically use a set of control parameters which have been determined through, for example, experimentation or calculation, to operate in an optimal manner to control the process variable. Although not the only possible technique, these control parameters are typically dependent on the anticipated range of differences ("error values") that result between the process variable and the set point during actual operation of the process.

Ordinarily, infusion formulation delivery systems utilize control systems having an input-response relationship. A system input, such as a sensed biological state, produces a physiological response related to the input. Typically, the input (such as a sensed blood glucose level) is used to control some parameter associated with the response variable (such as an insulin infusion rate or an amount of insulin).

A process controller employed in the delivery of an insulin formulation typically executes a closed-loop algorithm that accepts and processes a blood glucose level input supplied to the controller by a sensing device. The closed-loop algorithm may adjust insulin formulation delivery as a function of, for example, the rate of change over time of the sensed glucose level.

These closed-loop algorithms have many limitations. Some of these limitations result from the fact that a process controller employing a closed-loop algorithm to control the delivery of an insulin formulation may be restricted to only adding insulin formulation to the system. Once insulin formulation is added to the system, normally the controller cannot retrieve it.

Additional limitations result from the fact that certain parameters affecting glucose production may not be adequately compensated for by these closed-loop algorithms. For example, certain daily events may significantly affect glucose production levels in the human body. Thus, these events may also significantly affect the amount of insulin required to metabolize the glucose.

Exercise, for example, has been shown to lower blood glucose levels in the human body. Thus, exercise may result in a dip in blood glucose levels and a corresponding decrease in the amount of insulin formulation delivered by the body.

Longer or more strenuous exercise events may result in a greater dip in blood glucose level than shorter and less strenuous exercise events.

Similarly, sleep and stress may affect the body's ability to burn carbohydrates and therefore may affect glucose levels. For example, glucose metabolism has been found to be slower in a sleep deprived state. In addition, elevations of certain stress hormones within the body may also result in slower glucose metabolism. Thus, longer or shorter periods of sleep or stress may result in more or less significant changes in glucose levels.

Furthermore, the ingestion of certain medications may affect a user's sensitivity to insulin, i.e. a given amount of insulin may be more or less sufficient depending on whether or not a particular medication has been taken.

An additional event that may significantly affect the production of glucose in the body is the ingestion of food. This results in part from the fact that during digestion carbohydrates are broken down into glucose that then enters the bloodstream. In addition, the amount and type of foods ingested affect the amount of glucose produced.

Closed-loop algorithms employed for controlling delivery of an insulin formulation in response to sensed blood glucose levels may not adequately compensate for the affects such daily events may have on blood glucose levels. Thus, the diabetic person relying on such closed-loop algorithms may be at an increased risk of hypoglycemia and/or hyperglycemia.

SUMMARY OF THE DISCLOSURE

Therefore, it is an advantage of embodiments of the present invention to provide a closed-loop algorithm for controlling delivery of insulin formulation which more accurately calculates an infusion formulation delivery rate based on a level of blood glucose which is sampled in a body at predefined intervals.

It is a further advantage of embodiments of the present invention to provide a closed-loop algorithm for controlling delivery of insulin formulation which may be adjusted in real time to more accurately determine whether a blood glucose level is rising or falling over a predetermined interval.

It is a further advantage of embodiments of the present invention to provide safety limits for bolus delivery that may be compared with samples of blood glucose parameters at predefined intervals and which enable or disable bolus delivery based on the comparisons.

It is a further advantage of embodiments of the present invention to provide safety limits on the amount of insulin formulation that may be stored in an accumulator during a predefined time interval.

It is a further advantage of embodiments of the present invention to provide safety limits on the amount of insulin formulation that may be delivered to a user during a predefined time interval.

These and other advantages are accomplished according to embodiments of a closed-loop algorithm for use in conjunction with a process controller for delivering an infusion formulation. Components of the closed-loop algorithm calculate a present value of infusion formulation in a body as well as whether that value is rising or falling overall during a predefined time interval. The closed-loop algorithm includes an equation whose variables are programmable in real time. The variables may be used as control parameters which may be adjusted to adjust the algorithm to more accurately calculate the present value of infusion formulation in the body.

Preferred embodiments of the present invention provide a closed-loop algorithm for use with a proportional-derivative controller for delivering an insulin formulation which comprises an equation for calculating a proportional component, a derivative component, and a basal component of an amount of insulin formulation to be delivered based on a sensed blood glucose level. Control parameters within the closed-loop algorithm may be programmable in real time and may be adjusted to compensate for events which may significantly affect the blood glucose level.

Depending upon the context of use, the invention may include various combinations of these features which function together to provide both adjustable control parameters and safety limits on the delivery of infusion formulation in response to a detected biological state. Various embodiments of the invention include one or more of these features.

These and other objects, features, and advantages of embodiments of the invention will be apparent to those skilled in the art from the following detailed description of embodiments of the invention, when read with the drawings and appended claims.

DETAILED DESCRIPTION OF EMBODIMENTS OF THE INVENTION

In the following description of preferred embodiments, reference is made to the accompanying drawings which form a part hereof, and in which is shown by way of illustration specific embodiments in which the invention may be practiced. It is to be understood that other embodiments may be utilized and structural changes may be made without departing from the scope of preferred embodiments of the present invention.

Environment of Use

As discussed above, embodiments of the present invention relate to a closed-loop algorithm for use in conjunction with a process controller for controlling the delivery of an infusion formulation to a body based in part on a sensed biological state within the body.

Embodiments of the invention may be employed in various infusion environments including, but not limited to a biological implant environment. In preferred embodiments, the closed-loop algorithm is employed for use in conjunction with a delivery device such as an infusion pump utilized in an implant environment within a human body. However, other embodiments may be employed for use in other biological implant or non-implant environments, including but not limited to external infusion devices, pumps or the like.

Furthermore, in example embodiments described herein, the closed-loop algorithm is employed for use in conjunction with an infusion pump configured for delivery of an insulin formulation used to regulate glucose levels in a diabetic user. However, other embodiments may be employed in the delivery of other infusion formulations having other pharmacological properties.

Closed-Loop Control System

Figure 1:
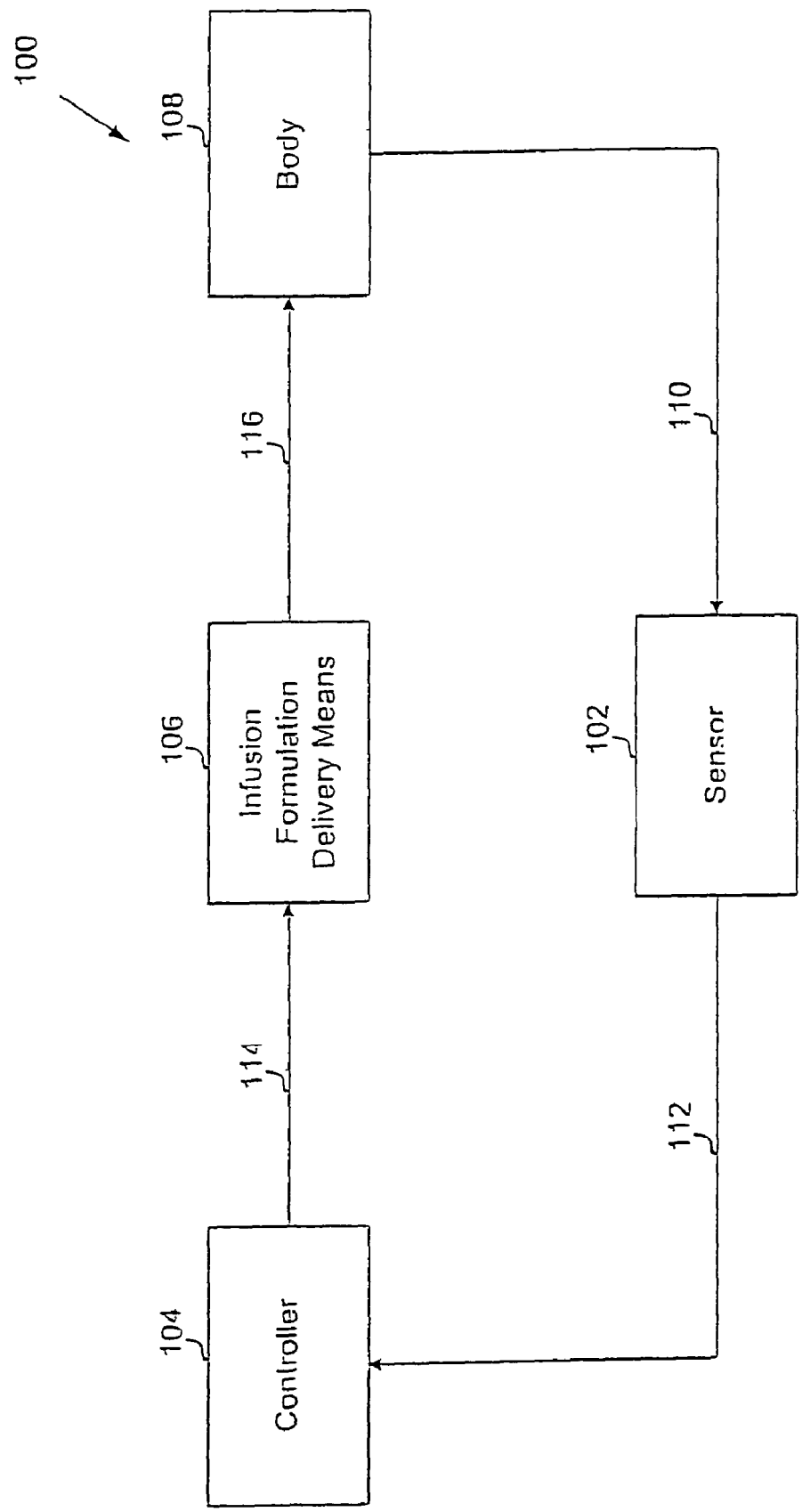
FIG. 1 shows a block diagram of an infusion formulation delivery system utilizing a control system having an input-response relationship, according to preferred embodiments of the invention.

A block diagram of an infusion formulation delivery system 100 utilizing a control system having an input-response relationship according to preferred embodiments of the invention is shown in FIG. 1. A sensor 102 generates a sensor signal 112 representative of a system parameter input 110 (such as a blood glucose level of a human body 108), and provides the sensor signal 112 to a controller 104. The controller 104 receives the sensor signal 112 and generates commands 114 that are communicated to the infusion formulation delivery device 106. The infusion formulation delivery device 106 then delivers the infusion formulation output 116 to the body 108 at a determined rate and amount in order to control the system parameter 110.

Sensor 102 may comprise a sensor, sensor electrical components for providing power to the sensor and generating the sensor signal 112, a sensor communication system for carrying the sensor signal 112 to controller 104, and a sensor housing for enclosing the electrical components and the communication system. Controller 104 may include one or more programmable processors, logic circuits, or other hardware, firmware or software components configured for implementing the control functions described herein, a controller communication system for receiving the sensor signal 112 from the sensor 102, and a controller housing for enclosing the controller communication system and the one or more programmable processors, logic circuits, or other hardware, firmware or software components. The infusion formulation delivery device 106 may include a suitable infusion pump, infusion pump electrical components for powering and activating the infusion pump, an infusion pump communication system for receiving commands from the controller 104, and an infusion pump housing for enclosing the infusion pump, infusion pump electrical components, and infusion pump communication system.

Closed-Loop Algorithm

Figure 2:
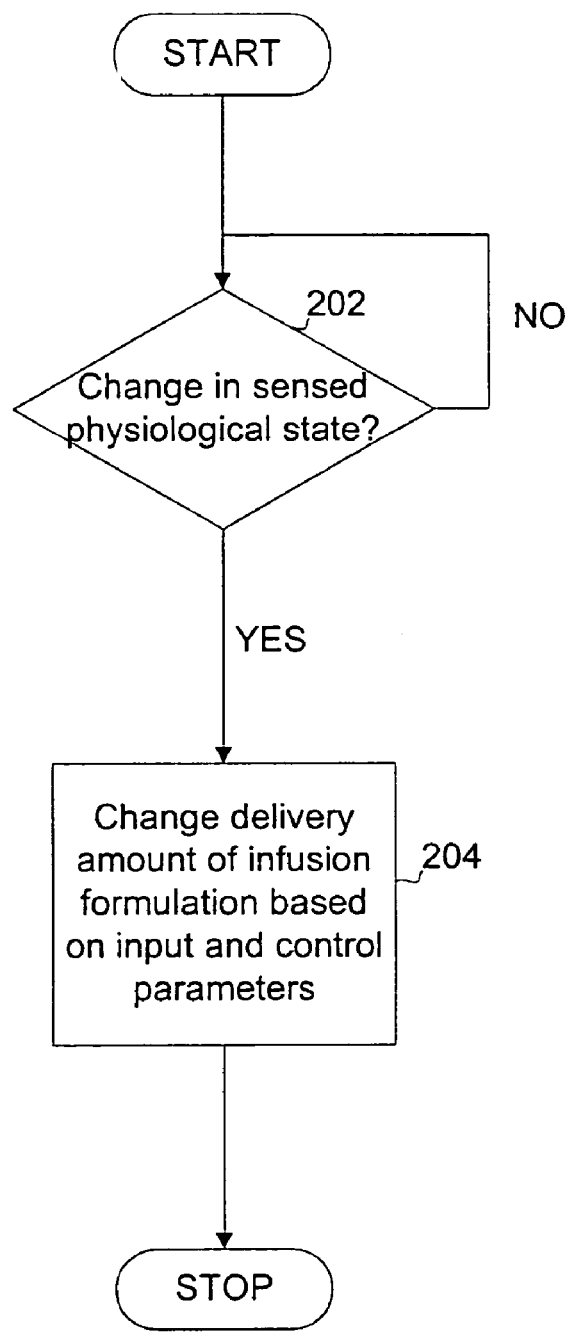
FIG. 2 shows a flow diagram of a general process performed by a closed-loop algorithm for adjusting infusion formulation delivery as a function of a change in a sensed biological state.

FIG. 2 shows a flow diagram of a general process performed by a closed-loop algorithm for adjusting infusion formulation delivery as a function of, for example, the rate of change over time of a sensed biological state. As shown in step 202, the closed-loop algorithm checks for changes in the biological state at timed intervals. A sensing device such as sensor 102 detects the change in glucose level and communicates the change to a control device such as controller 104 as an input to the closed-loop algorithm. If no change is detected, the closed-loop algorithm loops back to step 202, repeating this process until a change is detected. When a change occurs at step 204, the closed-loop algorithm determines the amount and/or rate of infusion formulation required based on the input and various parameters that have been programmed into the controller.

Where the infusion formulation delivery system 100 shown in FIG. 1 includes a controller 104 used for controlling an insulin response to a sensed blood glucose level, the closed-loop algorithm may be of the proportional-derivative (PD) type. The use of a PD type closed-loop algorithm is advantageous, for example, when processing resources such as processor power and/or memory may be limited. In alternative embodiments, a proportional-integral-derivative (PID) type closed-loop algorithm may be used.

PD controllers may utilize a closed-loop algorithm which computes both a proportional component and a derivative component of a response (output) to changes in a system parameter (input). For example, the proportional and derivative components may be combined to calculate an amount of insulin formulation to be delivered in response to a present sensed blood glucose level (system parameter input 110) within a body 108. The controller may then issue commands 114 to, for example, output a calculated amount of insulin formulation (output 116) to an infusion site on or within the body 108 based on the present sensed blood glucose level.

The magnitude of each component's contribution to the calculated amount of insulin formulation to be delivered to the infusion site may be expressed by a formula or equations, such as the following equations:

$$U_P = \alpha(G_{(t)} - G_{sp}) \quad \text{Equation 1}$$

and $$U_D = \beta dG/dt, \quad \text{Equation 2}$$

where
- $U_P$ is the proportional component of the response,
- $U_D$ is the derivative component of the response,
- $\alpha$ is a proportional gain coefficient,
- $\beta$ is a derivative gain coefficient,
- G is a present blood glucose level,
- $G_{sp}$ is a desired blood glucose level or "set point" for the blood glucose level, and
- t is the time at which the blood glucose level is sensed.

There is a desired blood glucose level $G_{sp}$ for each person which may be determined, for example, from experimentation or from the person's historical physiological data. The closed-loop control system may be designed to maintain the desired blood glucose level $G_{sp}$ for a particular person. It may do this, in part, by measuring the difference between the determined $G_{sp}$ and a blood glucose level G sensed at time t ($G_{(t)}$). This difference is the blood glucose level error at time t that must be corrected.

The proportional component expressed in Equation 1 determines whether the blood glucose level error is positive, negative, or zero, (i.e., whether $G_{(t)}$ is, respectively, higher, lower, or equal to $G_{sp}$). Thus, $G_{sp}$ is subtracted from $G_{(t)}$. If $G_{(t)}$ is higher than $G_{sp}$, the controller 104 may generate an insulin formulation delivery command 114 to drive the infusion formulation delivery device 106 to provide insulin formulation (output 116) to the body 108. If $G_{(t)}$ is lower than $G_{sp}$, the controller 104 may reduce or stop delivery of the insulin formulation to the body 108 by the infusion formulation delivery device 106. The result of subtracting $G_{sp}$ from $G_{(t)}$ is then multiplied by a proportional gain coefficient $\alpha$. The derivative component dG/dt expressed in Equation 2 determines if the blood glucose level is presently rising or falling and at what rate of change.

Thus, to determine the amount of infusion formulation to be delivered at any point in time ($I_{(t)}$), the following standard equation may be used:

$$I_{(t)} = \alpha(G_{(t)} - G_{sp}) + \beta dG/dt \quad \text{Equation 3}$$

where $I_{(t)}$ is the amount of insulin formulation to be delivered based on the sensed blood glucose level at time t.

Example Operation of a Closed-Loop Algorithm

Figure 3:
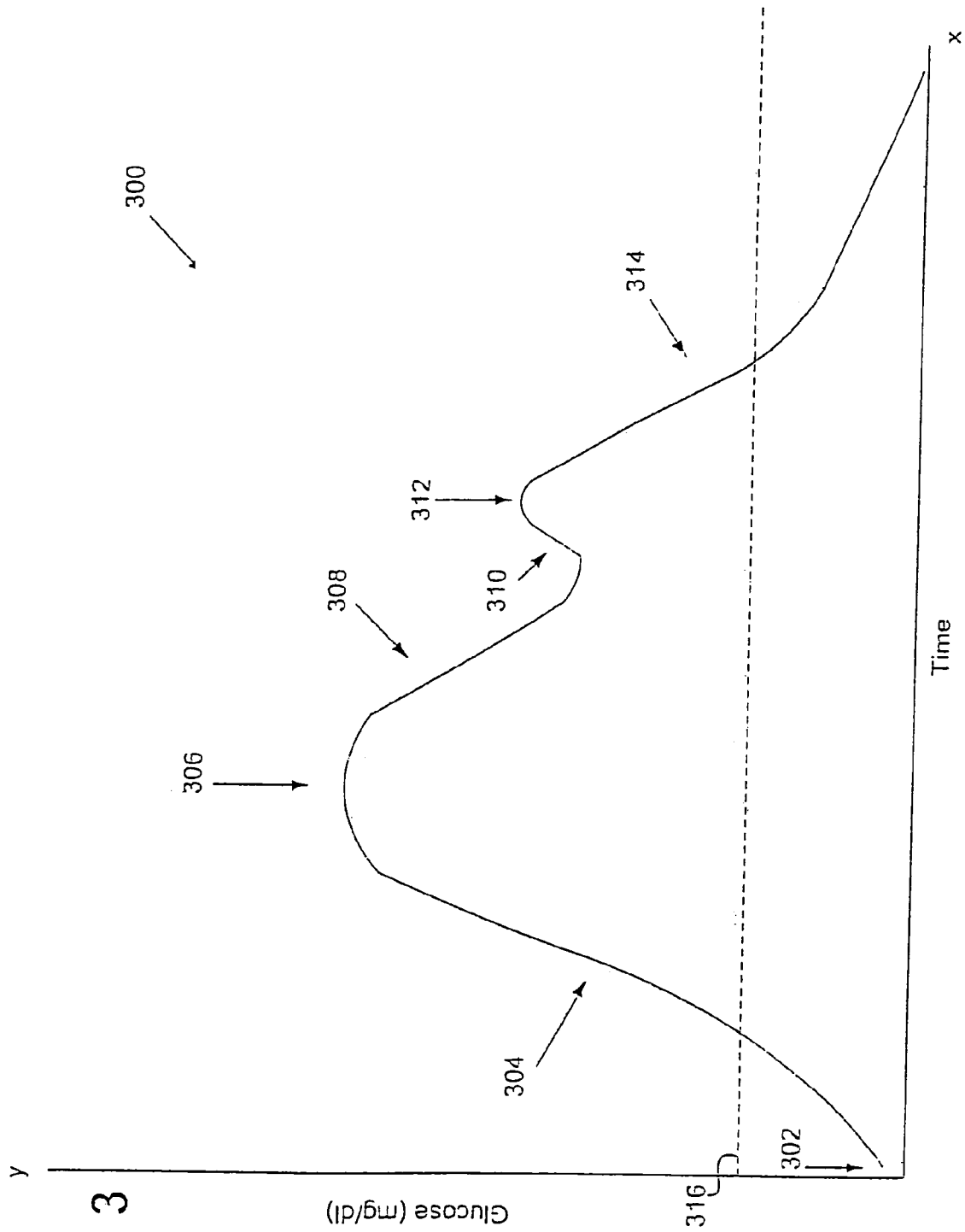
FIG. 3 shows the operation of a closed-loop algorithm used by a proportional-derivative controller.

Referring now to FIG. 3, the operation of a closed-loop algorithm used by a PD controller is described. FIG. 3 illustrates a typical human blood glucose response to the ingestion of a meal. Shown in FIG. 3 is a graph of a blood glucose response curve 300 (on the y axis) as a function of time (on the x axis). This blood glucose response curve 300 is representative of blood glucose levels sensed at various sampling times as a system parameter 110 by a sensor 102, as shown in FIG. 1.

As shown in FIG. 3, after a person ingests a meal 302, there is typically a steady rise 304 in blood glucose level over time until the blood glucose level reaches a peak 306. It has been observed from experimentation that peak 306 may occur approximately 90 minutes after ingestion of the meal. After peak 306 has been reached, it has been observed that the blood glucose level then begins to decrease 308 over time. During the decline from the first peak 306, a second temporary rise 310 in blood glucose level has been observed. A second peak 312 results from this temporary rise 310. This second peak 312 may occur approximately 30 to 90 minutes after the occurrence of peak 306 and typically tends to occur 30 to 60 minutes after the occurrence of peak 306.

After peak 312 has been reached, it has been observed that the blood glucose level then continues as before to decrease 314 over time. Although the reasons for this second, temporary rise 310 are not completely understood at the present time, it is a consistently observable phenomenon that presents a problem for a closed-loop algorithm.

To understand the problem, it is helpful to understand the response of a closed-loop algorithm at the various points of the response curve 300 shown in FIG. 3. As stated above, at point 302, the meal is ingested. As the blood glucose level rises 304 above the set point 316, a closed-loop algorithm may calculate both the amount by which the present blood glucose level exceeds the set point value (a proportional component) and may also determine that the blood glucose level is rising at a certain rate (a derivative component). Thus, a closed-loop algorithm may calculate a result based on these two components which causes a command to issue from a controller associated with the algorithm to deliver a calculated amount of insulin at a time t on the response curve 300 corresponding to 304.

At peak 306 of the response curve 300, the blood glucose level is neither rising nor falling, but the proportional component calculates that it is still above the set point and therefore the controller associated with the closed-loop algorithm may continue to issue commands to deliver more insulin formulation, although it may not be as large an amount as that issued at 304 on the response curve 300.

At 308, the proportional component calculates that the blood glucose level is still above the set point. However, now the blood glucose level is falling, and therefore the controller associated with the closed-loop algorithm may issue commands to deliver a decreased amount of insulin formulation based on the calculation of the derivative component.

At 310, the proportional component calculates that the blood glucose level is still above the set point. The derivative component will calculate that the blood glucose level is rising again. At this point, the controller associated with the closed-loop algorithm may issue a command to deliver another significant amount of insulin based on this information although, seen globally, the blood glucose level is decreasing overall. Thus, because of this additional input of insulin formulation into the system, the risks of hypoglycemia to the user are increased.

Embodiments of Closed-Loop Algorithms

Preferred embodiments of the present invention address the limitations of a closed-loop algorithm exemplified above in relation to FIG. 3. Preferred embodiments of closed-loop algorithms more accurately determine the amount of insulin formulation to be delivered based on a sensed blood glucose level by including programmable control parameters which may be used to introduce discontinuities in the calculation of $I_{(t)}$ unlike the continuous calculations of $I_{(t)}$ performed by the closed-loop algorithm described above. Embodiments of the present invention may be more effective at maintaining a desired blood glucose level for a particular user under circumstances where blood glucose level may be significantly affected by events such as, but not limited to meals, sleep, and exercise. As a result, the risk of hypoglycemia and/or hyperglycemia in the user may be reduced.

In some embodiments of the present invention, the derivative component of the closed-loop algorithm (dG/dt) shown in Equation 2 above is referred to as the "trend term" and may be expressed as:

$$\text{Trend term} = (G_{(t)} - G_{(t-x)})/x \qquad \text{Equation 4}$$

where x is a numerical value representing an increment of time.

In some embodiments, the value of the trend term is calculated at predetermined intervals, for example each minute, and is used to determine the "trend" of G, i.e., whether the value of G is trending up or trending down during a timeframe determined by the term (t−x). Thus, by changing the value of x, the timeframe for sampling the trend may be lengthened or shortened. As an example, using Equation 4, if x=10 minutes, the blood glucose level sensed 10 minutes prior in time to time t is subtracted from the blood glucose level sensed at time t. In some embodiments, as discussed in more detail below, the value of x may be programmable. In alternative embodiments, linear regression or other curve-fitting techniques may be used.

Generally, a shorter timeframe (and, thus, a smaller value of x) is preferred for trend calculation because the shorter the timeframe, the more responsive the infusion formulation delivery system may be to a rising or falling blood glucose level. However, this responsiveness must be balanced against noise susceptibility of the sensor signal, which may increase as the timeframe gets shorter. After the trend term is calculated, it is multiplied by the derivative gain coefficient β.

The proportional gain coefficient α and derivative gain coefficient β (β is also referred to in the present disclosure as the "trend gain") may be chosen based, for example, on experimentation. As an example, they may be chosen based on observations of the insulin response of several normal glucose tolerant users. An average of the values of these responses may then be taken. Alternatively, other statistical values besides an average value may be used, for example a maximum or minimum value, standard deviation value, or some other suitable value.

In some embodiments, as discussed in more detail below, both the proportional and derivative gain coefficients may be programmable. In addition, β may be programmed as one value when the trend is going up and a different value when the trend is going down (also referred to in the present disclosure as the "trend up" and "trend down" gains).

It is believed that even if $G_{(t)}$ is equal to $G_{sp}$ (in other words if the proportional component of the response is zero), a certain minimal amount of insulin formulation should still be delivered in order to maintain that condition. Thus, in some embodiments, in addition to Equation 1 and Equation 2 shown above, a basal insulin formulation delivery amount is included as a further component of the response. This basal component ($B_0$) represents, in some embodiments, a minimum amount of insulin formulation that would be delivered when $G_{(t)}$ is equal to or greater than $G_{sp}$ (i.e., when the blood glucose level at time t is equal to or greater than the desired blood glucose level or set point) and without regard to the rate at which the blood glucose level is rising or falling. In some embodiments, as discussed in more detail below, $B_0$ may be programmable and may be selected from a programmable table of multiple $B_0$ values based on certain criteria. By selecting $B_0$ values from this programmable table, different values of $B_0$ may be selected for different parts of the day (for example, dawn). Thus, different parts of the day may be treated differently than other parts of the day.

Thus, to determine the amount of infusion formulation to be delivered at any point in time ($I_{(t)}$) the following equation may be used by embodiments of the present invention:

$$I_{(t)} = \alpha(G_{(t)} - G_{sp}) + \beta((G_{(t)} - G_{(t-x)})/x) + B_0 \qquad \text{Equation 5}$$

Higher Order Filters for Down Trend

Generally, the body's blood glucose level changes slowly compared to the rate at which the sensor 102 samples these levels. Therefore, high frequency signal components are typically noise. Referring again to FIG. 1, in some embodiments of the present invention sensor 102 may further include a filter. The filter may be used to reduce noise seen in sensor signal 112 in particular frequency bands prior to being received by controller 104. In some embodiments, a low pass filter such as, but not limited to, a finite impulse response ("FIR") filter, is used for this purpose. This filter may be adjusted to pass lower frequencies and stop higher frequencies.

By increasing the order of the FIR filter, a sharper cutoff in the frequency response of the low pass filter may be achieved. In one embodiment of the present invention, the order of the filter may be programmable and different orders of the filter may be implemented based on whether the blood glucose level response curve (for example, response curve 300 in FIG. 3) is rising or falling.

Figure 4:
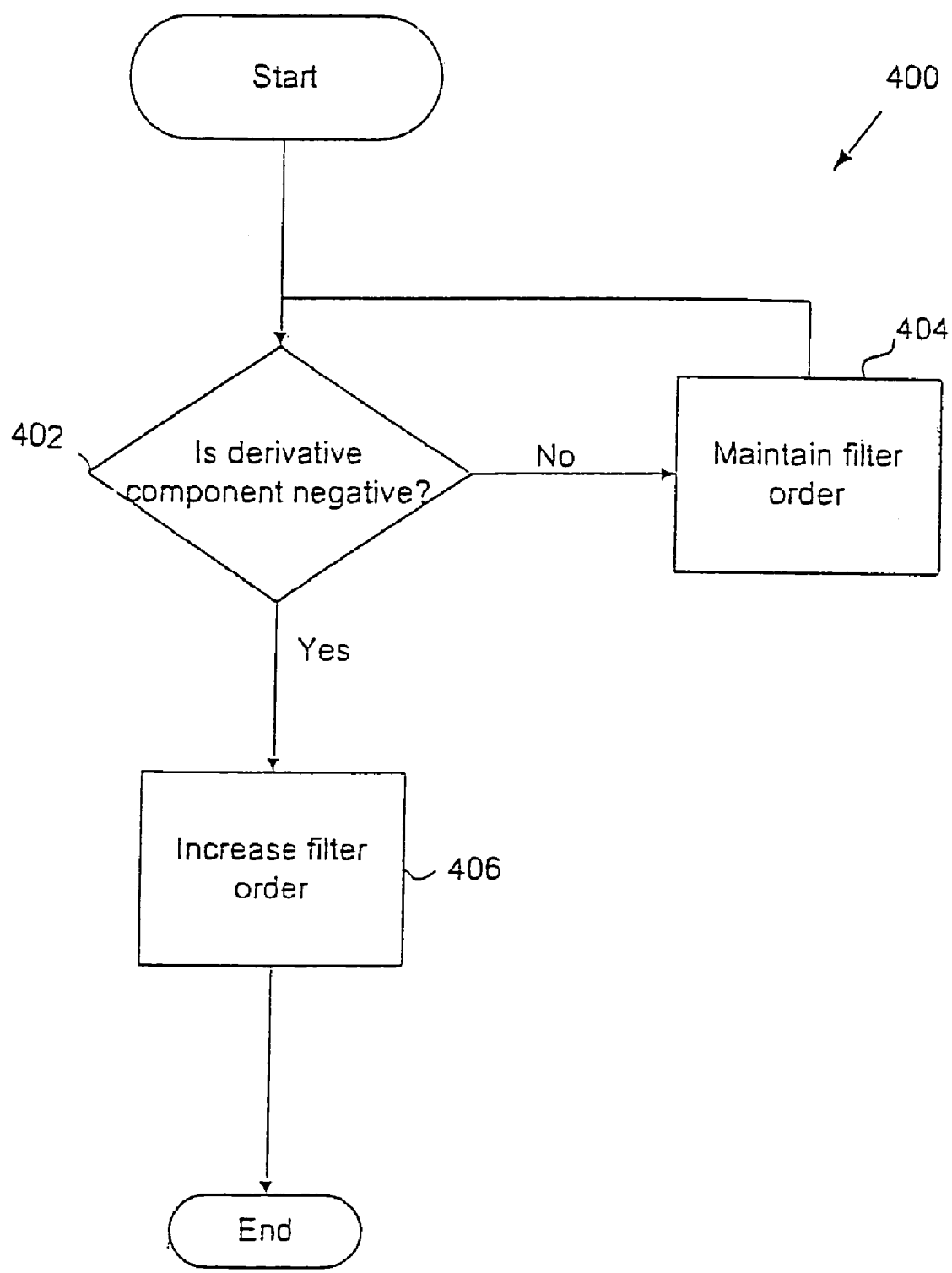
FIG. 4 shows a flow diagram 400 illustrating a process for implementing a filter order, according to an embodiment of the invention.

FIG. 4 shows a flow diagram 400 illustrating the process for implementing a filter order. As illustrated in flow diagram 400, in one embodiment the derivative component of Equation 5 may be sampled at step 402. If the derivative component of Equation 5 is a positive value or zero, i.e., if the blood glucose level is rising or at a peak, the filter order may be maintained as shown in step 404. If the derivative component of Equation 5 is a negative value, i.e., if the blood glucose level is falling, a higher order filter may be implemented at step 406. As a result of implementing a higher order filter when the blood glucose level is falling, the temporary peaks on the falling side of the response curve (such as peak 312 in FIG. 3) may be flattened, as illustrated in FIGS. 5A and 5B.

Figure 5A:
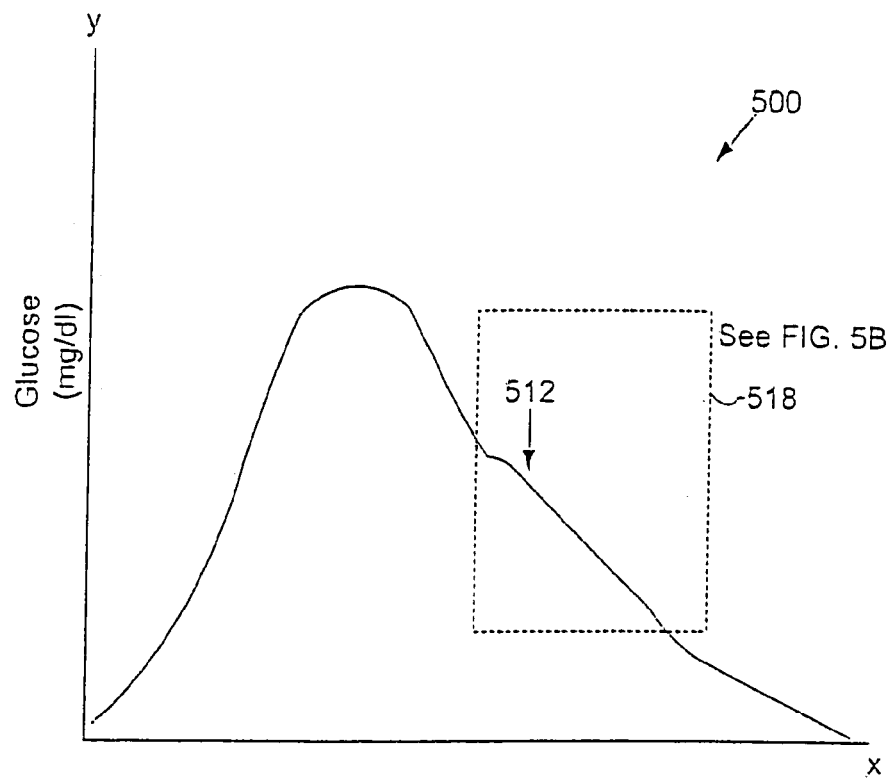
FIG. 5A shows a blood glucose response curve after a higher filter order for the falling side of the curve has been implemented, according to one embodiment of the present invention.
Figure 5B:
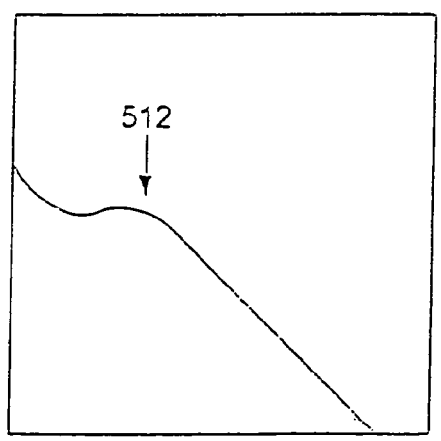
FIG. 5B shows a magnified view of a portion of the response curve of FIG. 5A.

FIGS. 5A and 5B illustrate the effects of this embodiment of the present invention on a response curve such as response curve 300. FIG. 5A shows a response curve 500 after the higher filter order for the falling side has been implemented according to one embodiment of the present invention described above. FIG. 5B shows a magnified view of a portion of the response curve referred to in FIG. 5A by numeral 518.

It can be seen from FIG. 5B that the second peak 512 (corresponding to second peak 312 in FIG. 3) has been flattened as a result of the higher order filter. Thus, the derivative component of the closed-loop algorithm may not detect as steep a rise and may reduce the amount of insulin formulation delivered as a result of this second peak 512. Therefore, as a result of implementing embodiments of the invention, the risk of hypoglycemia to the user may be reduced.

Disabling Closed-Loop Algorithm During Predefined Time Window

In another embodiment of the present invention, after a meal has been ingested by a user, the amount of insulin formulation to be delivered based on a sensed blood glucose level may be more accurately determined by establishing, for example from historical physiological data, a time window within which the temporary rise in blood glucose level occurs in the user. Once this time window has been established, embodiments of the present invention may disable any further commands from issuing from the controller (for example, commands 114 from controller 104 in FIG. 1), by, for example, programming start and stop times for the time window that may be used by the controller to suspend any further calculations of $I_{(t)}$ during the time window.

Figure 6:
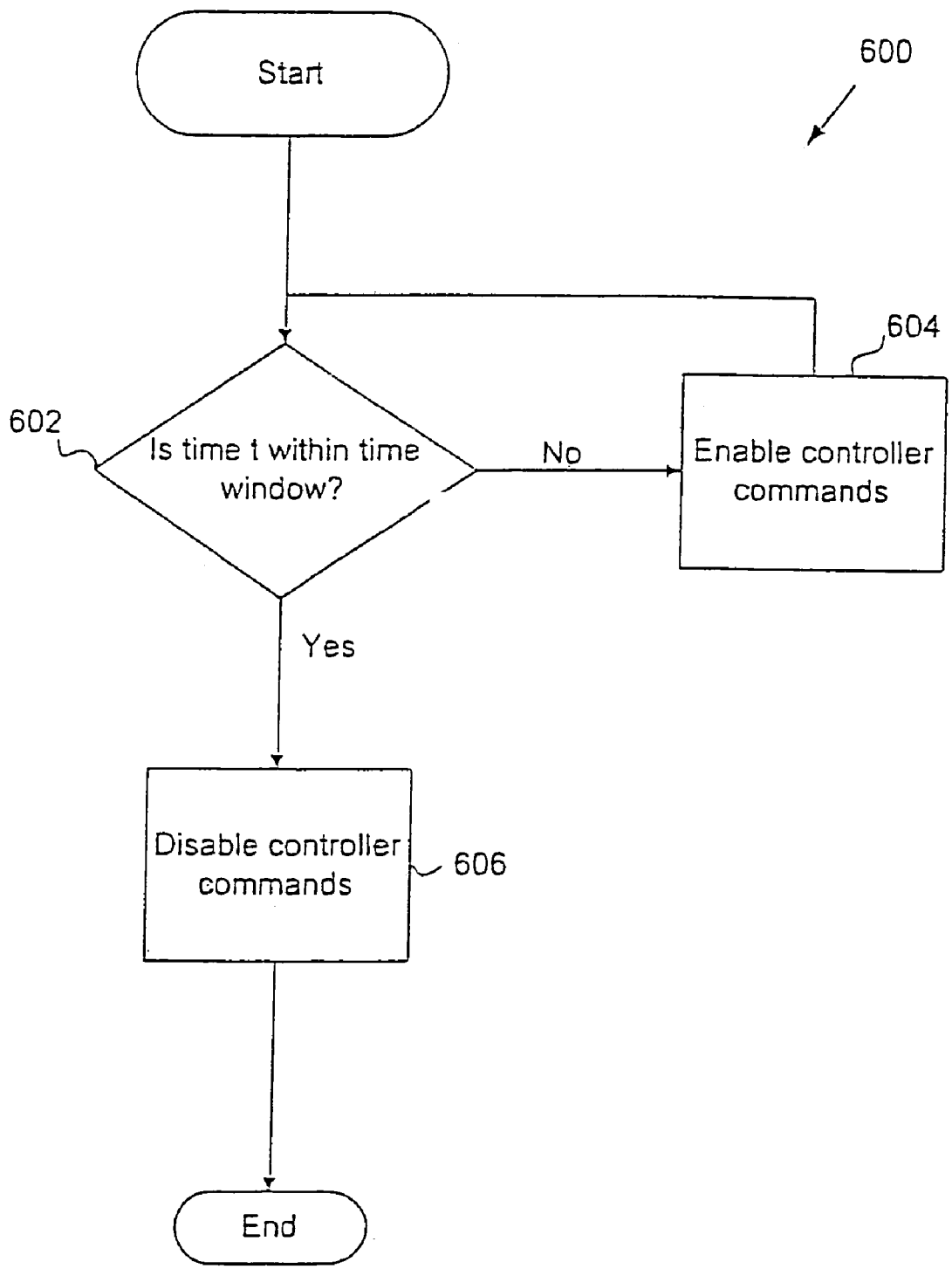
FIG. 6 shows flow diagram 600 to illustrate effects of implementing time windows, according to an embodiment of the invention.

FIG. 6 shows flow diagram 600 which illustrates the effects of implementing time windows, as described above. As illustrated in flow diagram 600, in one embodiment the current time t may be sampled and compared at step 602 to the programmed start and stop times to determine if time t is within the programmed time window. If time t is not within the programmed time window, the issuance of commands based on Equation 5 may be enabled at step 604. If time t is within the programmed time window, the issuance of commands based on Equation 5 may be disabled at step 606 until the programmed stop time. In this way, minimal or no additional insulin formulation may be delivered during the time window, as illustrated by the graph shown in FIG. 7.

Figure 7:
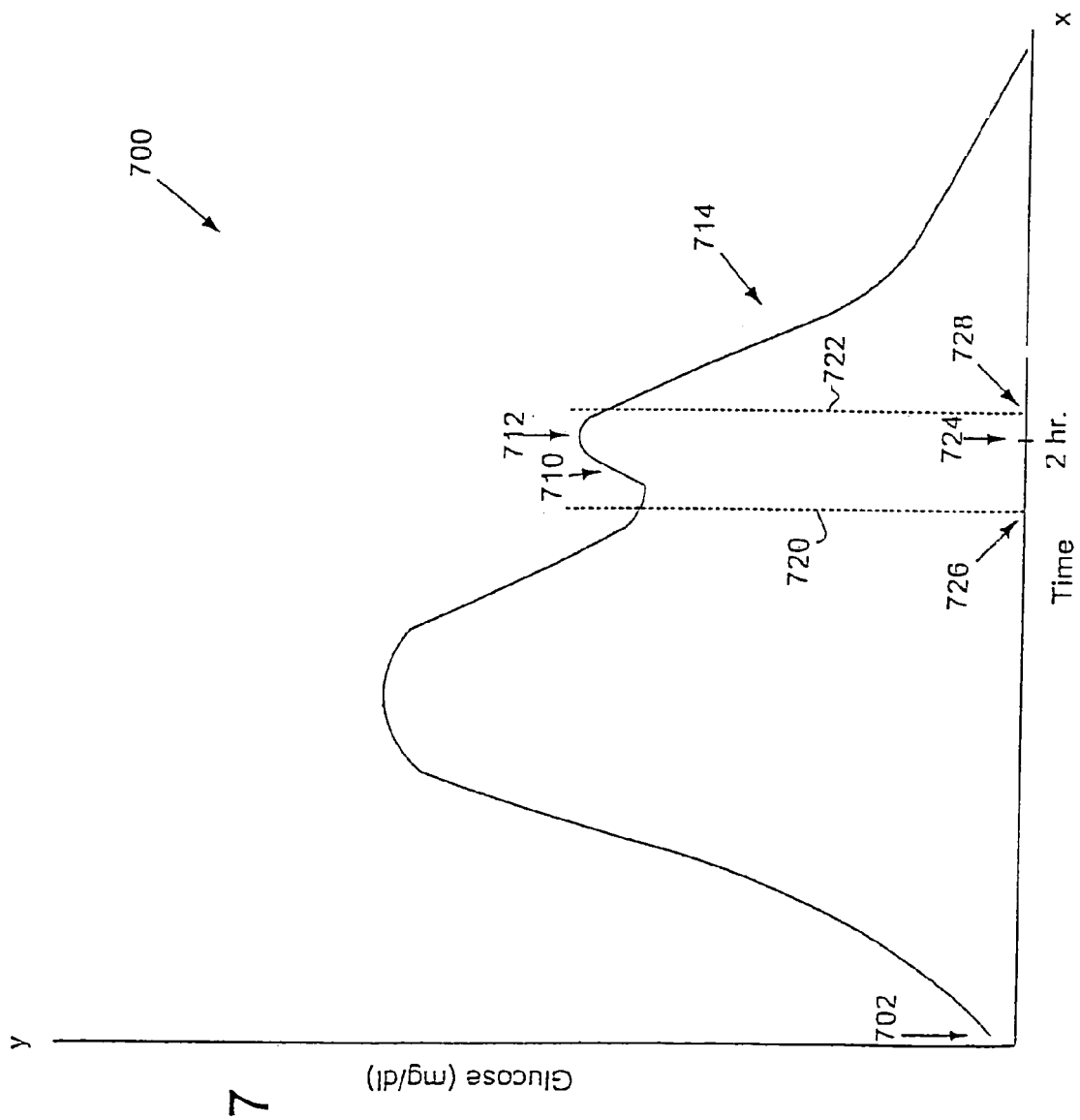
FIG. 7 shows a graph of a human blood glucose response for a user who has ingested a meal, illustrating effects of implementing a time window, according to an embodiment of the invention.

FIG. 7 shows a graph of a human blood glucose response 700 for a user who has ingested a meal at the point in time referred to by numeral 702. For the purposes of illustration, it will be assumed that it has been established from the user's historical physiological data that the second rise occurs in the user at the time referred to by numeral 724. Thus, in the present example, the second peak 712 occurs approximately two hours after the meal is ingested. Thus, the time window for disabling commands from being issued by the controller may be set between a disable start time, referred to by numeral 726, and a disable stop time, referred to by numeral 728. After time 728 is reached, the controller commands may again be enabled.

It can be seen from FIG. 7 that because the second rise 710 and resulting second peak 712 occur within the programmed time window, the second rise does not result in any increase in delivered insulin formulation. This discontinuity in the calculation of $I_{(t)}$ may thus cause $I_{(t)}$ to be calculated based only on the global downward trend of response curve 700. Therefore, as a result of implementing one embodiment of the invention, the temporary rise 710 does not cause any increase in the amount of delivered insulin formulation, and the risk of hypoglycemia to the user is reduced.

Programmable Control Parameters for Equation 5

In yet another embodiment of the present invention, the amount of insulin formulation to be delivered based on a sensed blood glucose level may be more accurately determined by having control parameters in Equation 5 which are programmable. In some embodiments, higher accuracy is achieved by including some control parameters which may be programmable in real time, i.e., while the closed-loop control system is in operation. Table 1 shows the control parameters within Equation 5 that may be programmable in different embodiments of the present invention. In some embodiments, all the control parameters shown in Table 1 are programmable. In one embodiment, the control parameters shown in Table 1 may be programmed in real time. Table 1 also includes example values for each control parameter.

TABLE 1

| Control Parameter | Value |
| --- | --- |
| Glucose Set Point ($G_{sp}$) | 100 mg/dl |
| Basal Rate ($B_0$) | 0.5 units/hour |
| Proportional Gain ($\alpha$) | 0.01 units/hour |
| Trend Term | 2 mg/dl/minute |
| Trend Up Gain ($\beta$) | 1.0 units/hour * (mg/dl/minute) |
| Trend Down Gain ($\beta$) | 3.0 units/hour * (mg/dl/minute) |

Some embodiments of the present invention use the programmable control parameters shown in Table 1 to advantageously adjust the closed-loop algorithm to compensate for changes in the blood glucose level that result from events such as, but not limited to, a meal event. The temporary rise in blood glucose level seen a period of time after the meal has been ingested is an example of a change in blood glucose level resulting from an event. Other events that may require compensation for changes in the blood glucose level include, but are not limited to exercise, illness, stress, sleep and other events which may induce metabolic changes. Some embodiments may adjust the control parameters to compensate for the temporary rise so that it does not result in the delivery of a significant amount of insulin formulation. Thus, these embodiments decrease the risks of hypoglycemia to the user.

In one embodiment, the timeframe of the trend term of Equation 4 may be lengthened by increasing the programmable value of x. This embodiment is illustrated by the graph shown in FIG. 8, which shows a human blood glucose response 800 for a user who has ingested a meal at the point in time referred to by numeral 802. A first timeframe wherein x=10 minutes is referred to by numeral 804 and defines a 10 minute timeframe extending back in time from time t. It can be seen that if a trend term is calculated at time t, the trend of the blood glucose level will be calculated as rising 808 for that defined timeframe.

By increasing the value of x in the trend term, the timeframe may be lengthened in order to decrease the responsiveness of the infusion formulation delivery system and calculate a trend term that is more accurate in terms of whether the blood glucose level is globally rising or falling.

This is illustrated by a second timeframe, referred to by numeral 806, wherein x=30 minutes and defines a 30 minute timeframe extending back in time from time t. It can be seen that for the majority of the period encompassed by timeframe 806 the blood glucose level is trending downward. Thus, the overall calculation of the trend term will result in a negative value. Thus, by increasing the programmable value of x in order to define a longer timeframe in which to sample the trend, a more accurate calculation is made of $I_{(t)}$, thus reducing the risk of hypoglycemia to the user.

In a further embodiment, the value of x in the trend term of Equation 4 may be increased only for the falling side of blood glucose response curve 800. Thus, in this embodiment, the controller may be programmed to increase the value of x in the trend term of Equation 4 when the trend term first indicates that the blood glucose level is falling. In this manner, the better responsiveness of the shorter timeframe may be maintained while the blood glucose level is rising.

Figure 9:
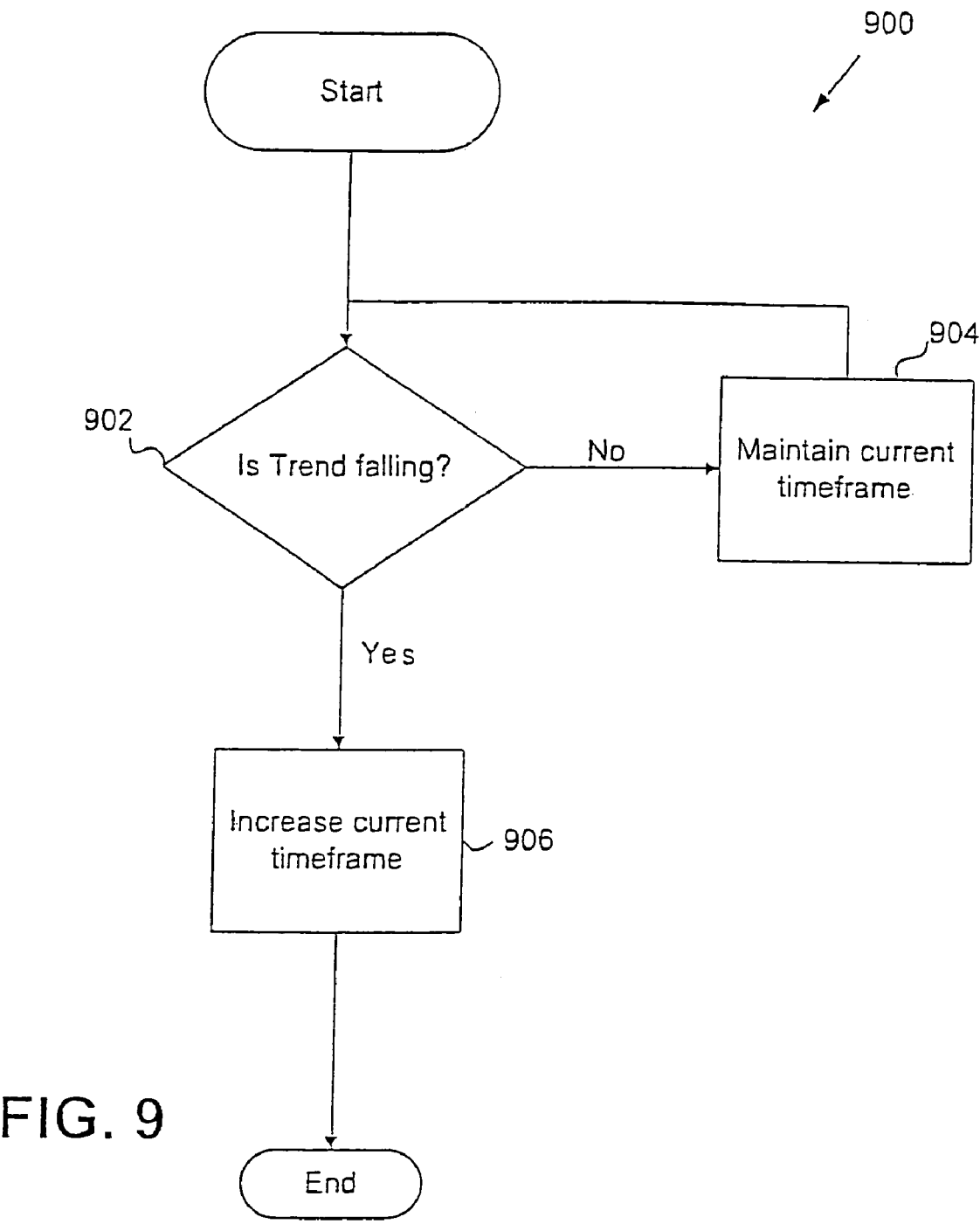
FIG. 9 shows flow diagram which illustrates effects of increasing the value of x in the trend term of Equation 4 when the trend term first indicates that the blood glucose level is falling, according to an embodiment of the invention.

FIG. 9 shows flow diagram 900, which illustrates effects of increasing the value of x in the trend term of Equation 4 when the trend term first indicates that the blood glucose level is falling. The trend may be sampled at step 902 at time t and it may be determined whether or not the trend is falling. If the trend is not falling, the timeframe may be maintained, as shown at step 904. If the trend is falling, the timeframe may be increased, as shown at step 906. In this way, the trend control parameter of the closed-loop algorithm may be adjusted in such a way that the temporary rise in the blood glucose level may have no effect on the overall, global trend of the blood glucose level over time.

Figure 8:
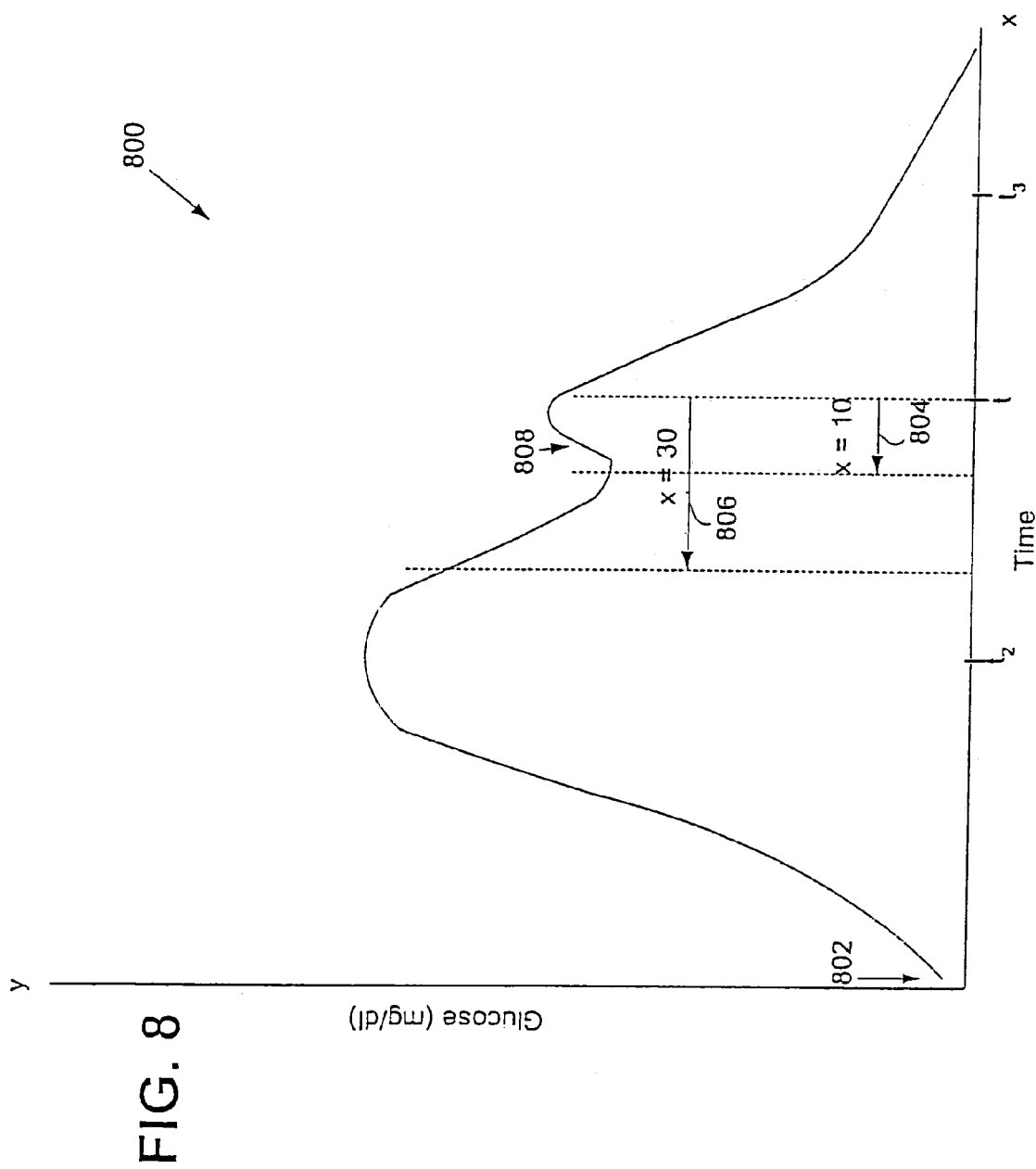
FIG. 8 shows a graph of a human blood glucose response for a user who has ingested a meal, illustrating effects of implementing time windows, according to an embodiment of the invention.

Thus, the embodiment illustrated in FIG. 8 uses the programmable trend term parameter shown in Table 1 to advantageously adjust the closed-loop algorithm such that the temporary rise in blood glucose level does not result in the delivery of a significant amount of insulin formulation and thus reduces the risks of hypoglycemia to the user.

In other embodiments of the present invention, the trend up and trend down gain control parameters may be used to advantageously adjust the closed-loop algorithm such that the temporary rise in blood glucose level does not result in the delivery of a significant amount of insulin formulation. As stated above, the trend gain control parameter β may be chosen based on observations of the insulin response of several normal glucose tolerant users.

It has been determined through experimentation that the risk of hypoglycemia may be reduced by rapidly cutting off insulin formulation delivery to the user once it is determined that the trend is falling. In some embodiments, therefore, the trend gain may be programmable and may have a greater value when the trend is falling (trend down gain) and a lesser value when the trend is rising (trend up gain).

Figure 10:
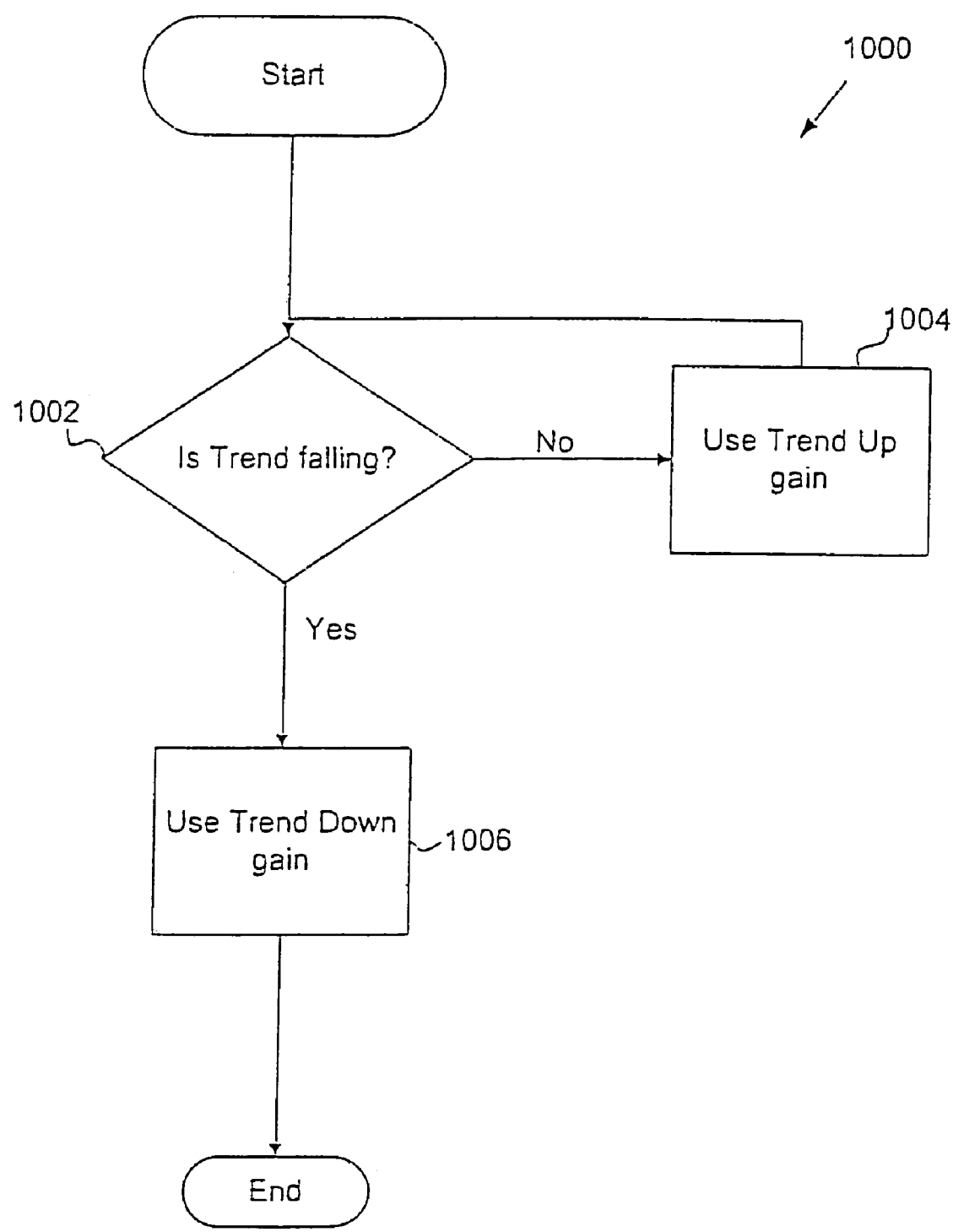
FIG. 10 shows a flow diagram illustrating effects of a programmable trend gain on the present calculated value of the infusion formulation, according to an embodiment of the invention.

FIG. 10 shows a flow diagram 1000 illustrating the effects of a programmable trend gain. The trend may be sampled at step 1002 at time t and it may be determined whether or not the trend is falling. If the trend is not falling, the trend up gain may be used in Equation 5, as shown at step 1004. If the trend is falling, the trend down gain may be used in Equation 5, as shown at step 1006. In this way, the trend gain control parameter of the closed-loop algorithm may be adjusted in such a way that the temporary rise in the blood glucose level may have no effect on the overall, global trend of the blood glucose level over time.

Figure 11:
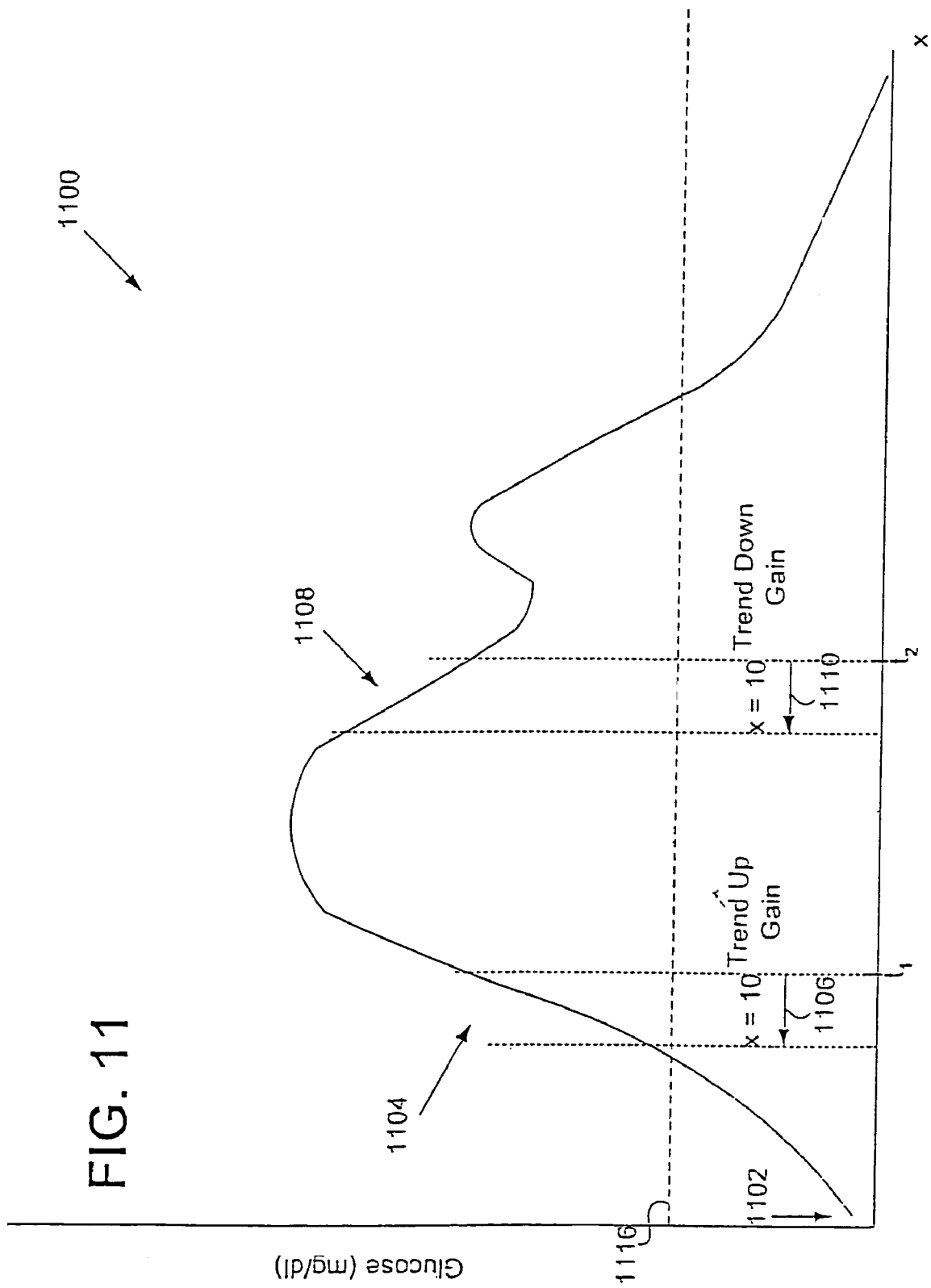
FIG. 11 shows a graph of a human blood glucose response for a user who has ingested a meal, illustrating a trend up gain and a trend down gain, according to an embodiment of the invention.

FIG. 11 illustrates why this may be advantageous in preventing the delivery of a significant amount of insulin formulation in response to the temporary, second rise in blood glucose level seen after a meal. FIG. 11 shows a graph of a human blood glucose response 1100 for a user who has ingested a meal at the point in time referred to by numeral 1102. Also shown in FIG. 11 is a timeframe, referred to by numeral 1106, wherein x=10 minutes and defines a 10 minute timeframe extending back in time from time t.

At time $t_1$, the trend of the blood glucose level is sampled and is determined to be rising 1104. Thus, the trend term will be some positive value. As an example, the trend term may have a value of 2 mg/dl/minute, as shown in Table 1 above. As seen in Equation 5, this value will be multiplied by the trend gain, and because it is positive, the trend up gain will be used. In this example, the trend up gain is chosen as 1.0 units/hour*(mg/dl/minute), as shown in Table 1. Thus, the derivative component of Equation 5 may be calculated as 1.0 units/hour*(mg/dl/minute)*2 mg/dl/minute=2 units/hour. It can be seen, therefore, that because, in the present example, the trend is rising at a rate of 2 mg/dl/minute, an additional 2 units/hour of insulin formulation is added to the proportional component and the basal component of Equation 5.

In contrast, when the trend is falling, a larger value of trend gain, i.e., the trend down gain, is used. Shown in FIG. 11 is a timeframe, referred to by numeral 1110, wherein x=10 minutes and defines a 10 minute timeframe extending back in time from time t. At time $t_2$ the trend of the blood glucose level is sampled and is determined to be falling 1108. Thus, the trend term will be some negative value. As an example, the trend term may have a value of −2 mg/dl/minute, as shown in Table 1 above. As seen in Equation 5, this value will be multiplied by the trend gain, and because it is negative, the trend down gain is used. In this example, the trend down gain is chosen as 3.0 units/hour*(mg/dl/minute), as shown in Table 1. Thus, the derivative component of Equation 5 may be calculated as 3.0 units/hour*(mg/dl/minute)*−2 mg/dl/minute=−6 units/hour. It can be seen, therefore, that because in the present example the trend is falling at a rate of 2 mg/dl/minute, it is calculated that 6 units an hour should be subtracted from the current insulin formulation delivery rate.

In some embodiments, the trend down gain may be chosen such that the calculation of the derivative component of Equation 5 results in a high enough negative value to completely offset the other components of Equation 5 and, thus, to substantially cut off further delivery of insulin formulation during the down trend, even though the blood glucose level is currently above the set point 1116. Thus, embodiments may use a high enough value for the trend down gain such that the temporary rise in blood glucose level may have no effect, since the delivery of insulin formulation may be cut off at a time t before the temporary rise occurs. Thus, the risk of hypoglycemia to the user is reduced.

In other embodiments of the present invention, the closed-loop algorithm advantageously disables the trend term from contributing to $I_{(t)}$ under certain circumstances in order to further reduce the risks of hypoglycemia to a user. In one embodiment, the trend term of Equation 5 is disabled and does not contribute to $I_{(t)}$ unless the trend is rising and the user's goal blood glucose level has been reached.

Figure 12:
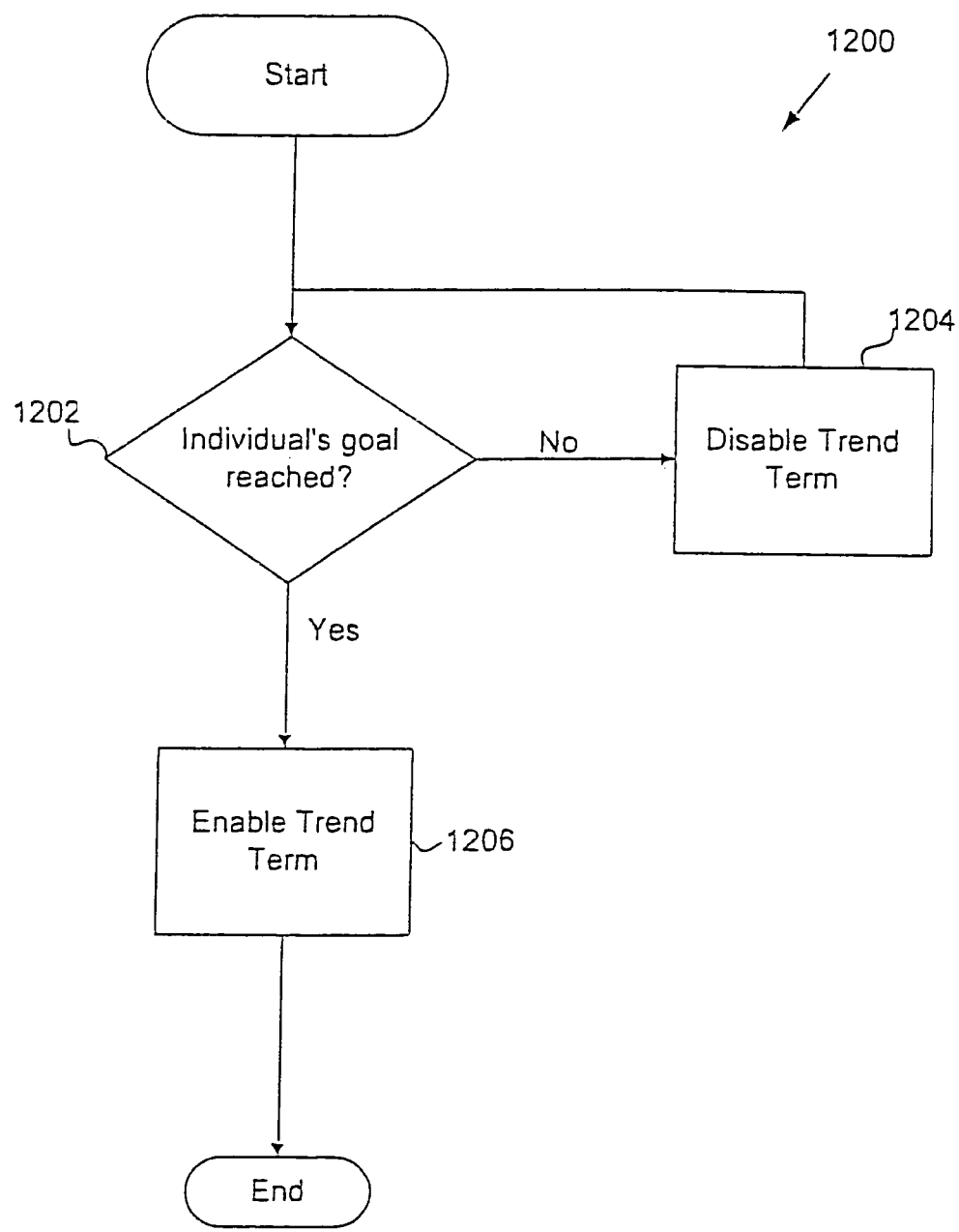
FIG. 12 shows a flow diagram illustrating effects of disabled and enabled trend terms, according to an embodiment of the invention.

This is illustrated in flow diagram 1200 shown in FIG. 12. The blood glucose level may be sampled at step 1202 and it may be determined whether or not the user's goal (set point) has been reached. If the goal has not been reached, the trend term may be disabled, as shown at step 1204. If the goal has been reached, the trend term may be enabled, as shown at step 1206. In this way, the closed-loop algorithm may be adjusted in such a way that a significant amount of insulin formulation may not be delivered to the user unless the user's blood glucose level is both rising and, at the same time, above the user's blood glucose level set point, thus reducing the risk of hypoglycemia.

Figure 13:
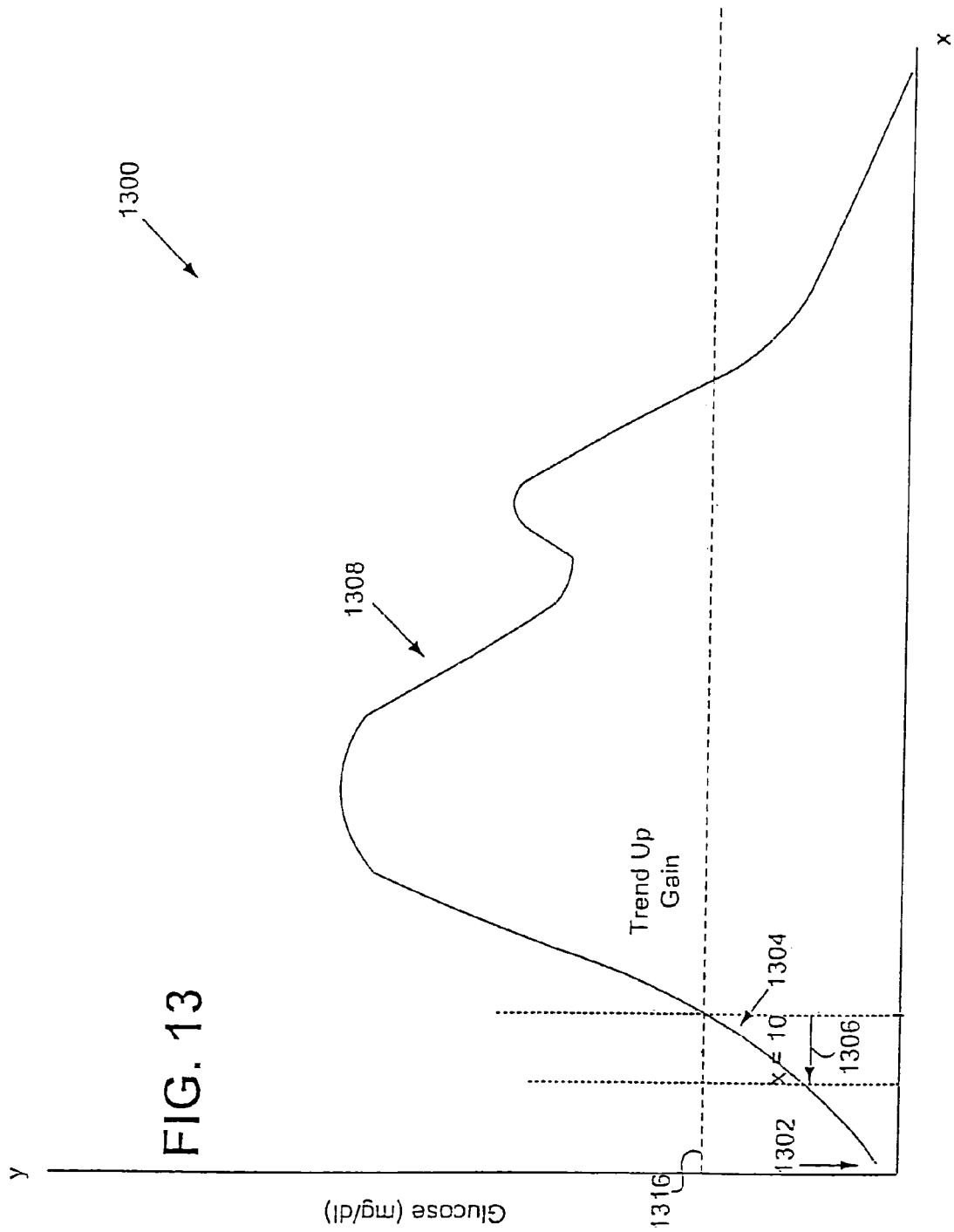
FIG. 13 shows a graph of a human blood glucose response for a user who has ingested a meal, illustrating effects of disabled and enabled trend terms, according to an embodiment of the invention.

FIG. 13 illustrates one embodiment. FIG. 13 shows a graph of a human blood glucose response 1300 for a user who has ingested a meal at the point in time referred to by numeral 1302. The blood glucose level begins to rise 1304, but is still below the user's set point value 1316. Thus, in one embodiment the derivative component of Equation 5 is disabled and does not contribute to $I_{(t)}$. When the blood glucose level reaches the set point 1316 at time t, the derivative component of Equation 5 is enabled and begins to contribute to $I_{(t)}$.

Shown in FIG. 13 is a timeframe, referred to by numeral 1306, wherein x=10 minutes and defines a 10 minute timeframe extending back in time from time t. At time t the trend of the blood glucose level may be sampled to determine the difference between the blood glucose level at time t and at time t−10, as described above in relation to FIG. 11. Therefore, once the user's blood glucose level is both rising and above the set point, the trend term of Equation 4 (which is equivalent to the derivative component of Equation 5) may be calculated. An additional amount of insulin formulation determined by the calculation may then be delivered to the user to assist in metabolizing the blood glucose.

In other embodiments of the present invention, the closed-loop algorithm advantageously enables and disables the basal bate $B_0$ component of Equation 5, which may be a programmable control parameter (as shown in Table 1 above). In one embodiment, the basal rate component may be enabled or disabled based in part on whether the user's blood glucose level is above or below, respectively, the user's set point.

As discussed above, the basal rate component $B_0$ of Equation 5 represents, in some embodiments, a minimum amount of insulin formulation that would be delivered when the blood glucose level at time t is equal to or greater than the desired blood glucose level or set point and without regard to the rate at which the blood glucose level is rising or falling. Embodiments advantageously disable the basal rate component $B_0$ of Equation 5 from contributing to $I_{(t)}$ when the blood glucose level falls below the set point and the trend term is falling. This may be done, for example, to substantially inhibit any further delivery of insulin formulation when the blood glucose level has fallen from a maximum value to a point below the set point.

Figure 14:
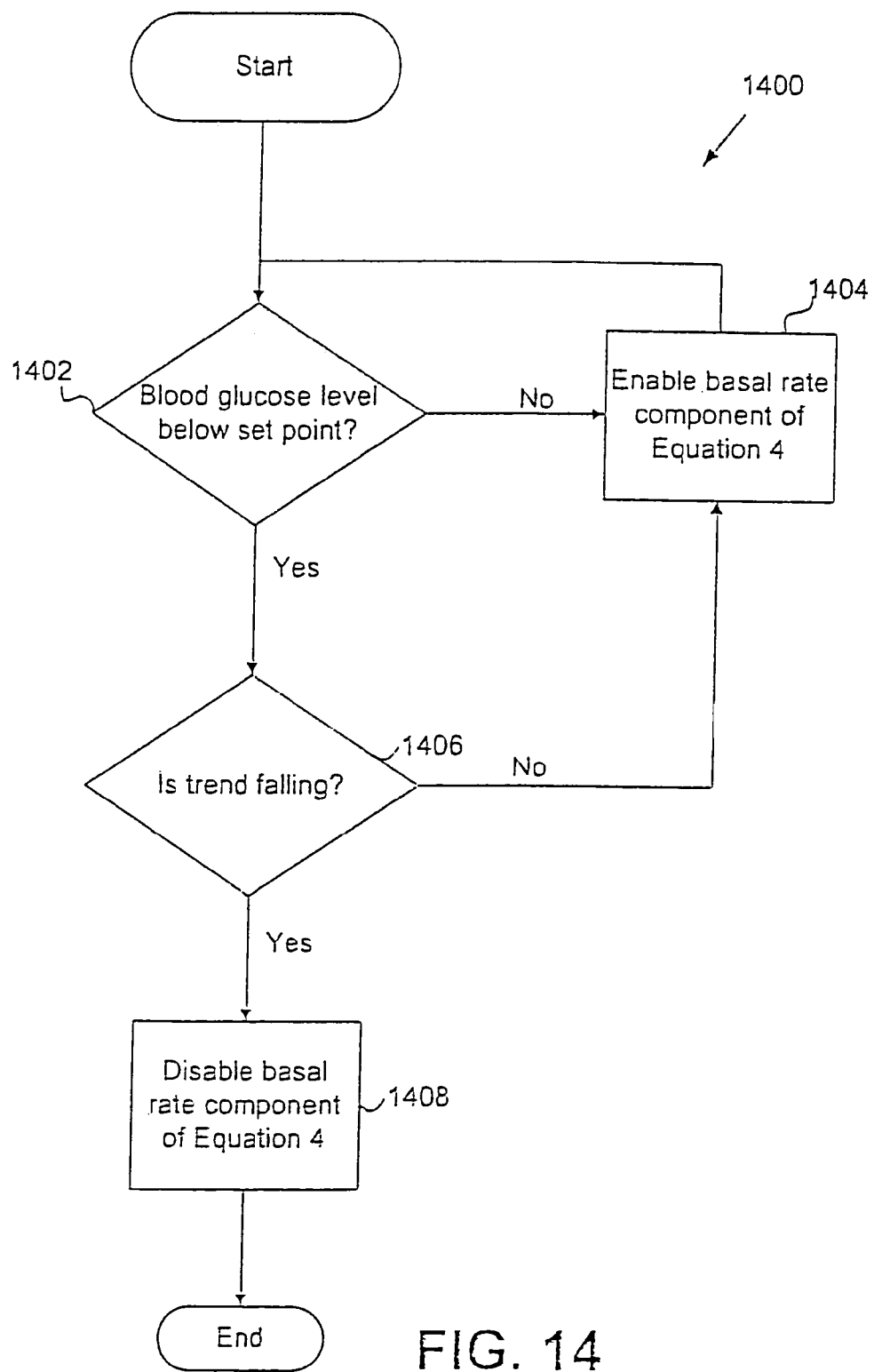
FIG. 14 shows a flow diagram illustrating effects of the basal rate component, according to an embodiment of the invention.

FIG. 14 shows a flow diagram 1400, illustrating the effects of the basal rate component of Equation 5. The blood glucose level may be sampled at step 1402 and it may be determined whether or not the user's blood glucose level is below the set point. If the blood glucose level is not below the set point, the basal rate component of Equation 5 may be enabled, as shown at step 1404. If the blood glucose level is below the set point, the trend may be sampled and it may be determined whether or not the trend is falling, as shown at step 1406. If the trend is not falling, the basal rate component of Equation 5 may be enabled, as shown at step 1404. If the trend is falling, the basal rate component of Equation 5 may be disabled, as shown at step 1408. In this way, the basal rate component of Equation 5 would be enabled when the blood glucose level sampled at time t is equal to or greater than the set point value regardless of the trend direction and would be disabled when the blood glucose level sampled at time t is less than the set point value and the trend is falling.

Figure 15:
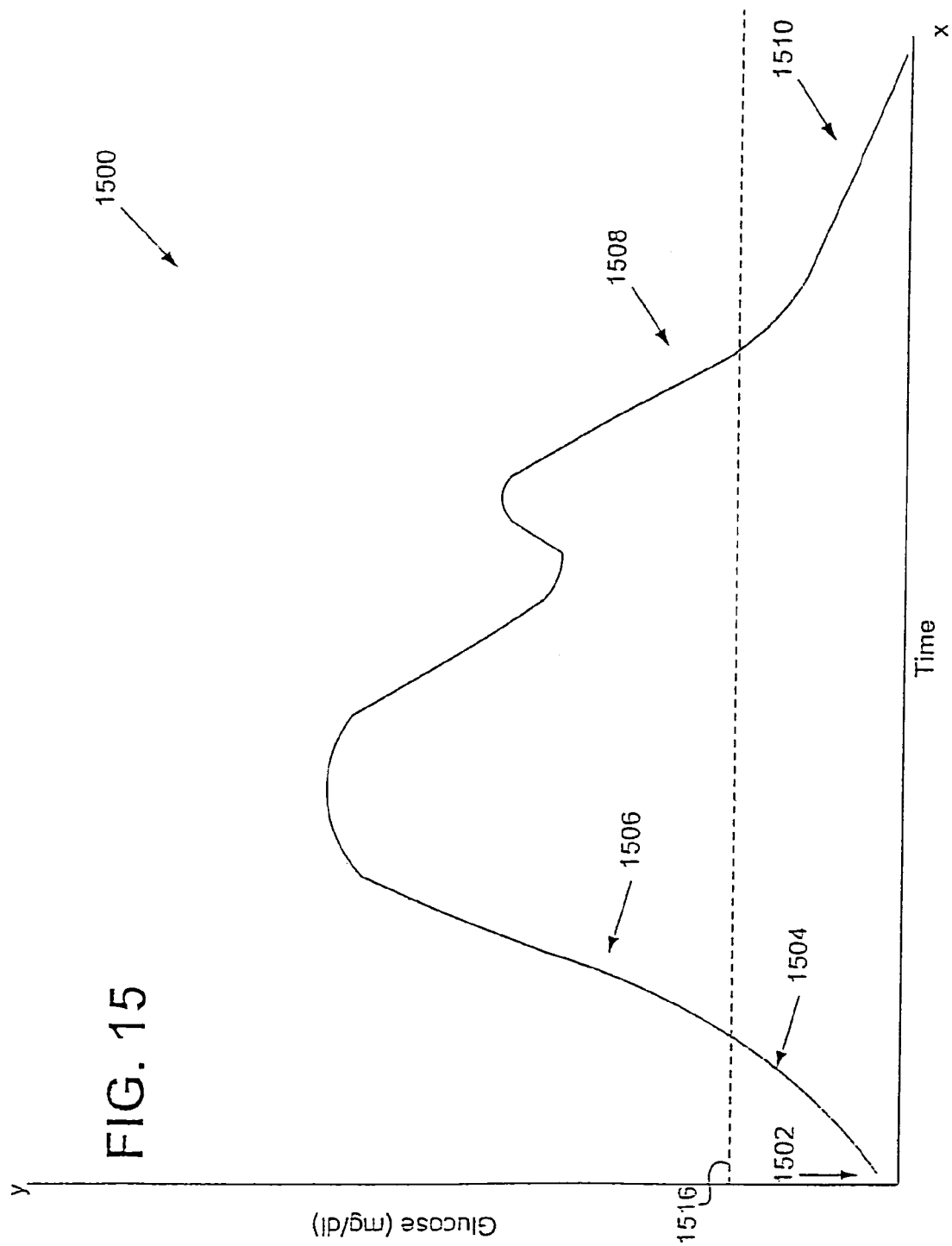
FIG. 15 shows a graph of a human blood glucose response for a user who has ingested a meal, illustrating effects of the basal rate component, according to an embodiment of the invention.

FIG. 15 illustrates one embodiment. FIG. 15 shows a graph of a human blood glucose response 1500 for a user who has ingested a meal at the point in time referred to by numeral 1502. The blood glucose level begins to rise 1504, but is below the user's set point 1516. Thus, according to the one embodiment, even though the user's blood glucose level is below the set point 1516, the basal rate component of Equation 5 is enabled because the trend is not falling. The blood glucose level is still rising at 1506 and is now above the user's set point 1516. Thus, because the user's blood glucose level is both above the set point 1516 and rising, the basal rate component of Equation 5 is enabled. According to one embodiment, under the conditions described above in relation to 1504 and 1506, the basal rate component of Equation 5 is enabled and contributes to $I_{(t)}$.

At 1508, the blood glucose level is falling, but is above the user's set point 1516. Thus, even though the user's blood glucose level is falling, it is still above the set point 1516 and, therefore, the basal rate component of Equation 5 is enabled. At 1510, the blood glucose level is still falling and is now below the set point. Thus, because the blood glucose level is both falling and below the set point, the basal rate component of Equation 5 is disabled and does not contribute to $I_{(t)}$. Therefore, one embodiment substantially cuts off any insulin formulation, including the basal rate component, when the glucose level is both falling and below the set point. In this way, embodiments reduce the risk of hypoglycemia.

Further embodiments of the present invention may include a programmable table of basal rate values. The closed-loop algorithm may be programmable to select particular basal rate values from the table to be used in calculating $I_{(t)}$ in Equation 5, for example, at particular times of the day. As an example, a different basal rate value may be selected at particular time intervals throughout the day. In one embodiment, the basal rate value may be updated every 30 minutes. In further embodiments, other control parameters within the closed-loop algorithm may be adjusted differently at different times of the day.

Thus, embodiments may advantageously adjust the basal rate based on daily events such as, but not limited to, meals, sleep, exercise, stress inducing events, ingested medications, and the like. In addition, embodiments enable the updating of basal rate values based on a particular user's historical physiological data. For example, a particular user may have a lower need for insulin at night. For that user the closed-loop algorithm may be programmed to use lower basal rate values at night.

Monitoring Biological States Other Than Blood Glucose Level

In further embodiments of the present invention, the amount and/or rate of delivered insulin formulation may modified based on inputs from sensing devices that detect other biological states in lieu of or in addition to the sensed blood glucose level. For example, it has been observed that a user's blood oxygen levels may change based on whether the user is awake or sleeping. As discussed above, sleep is an event which may significantly affect blood glucose levels in particular users. Thus, embodiments may sense the blood oxygen level of a user to determine if the user is asleep and input this information to the closed-loop algorithm in order to adjust the amount and/or delivery rate of insulin formulation based on this information.

Similarly, it has been observed that body temperature may significantly affect blood glucose levels. Thus, one embodiment includes a temperature sensor which monitors body temperature and includes this information as an input to the controller in order to adjust the amount and/or delivery rate of insulin formulation based on this information.

Further embodiments of the present invention may include a sensing device for detecting whether or not a user is exercising. In one embodiment, an accelerometer or other device suitable for detecting motion may be used to detect motion as an indicator of current physical activity. As discussed above, exercise may significantly affect blood glucose levels in particular users. Thus, information from the exercise sensing device may be input to the controller in order to adjust the amount and/or delivery rate of insulin formulation based on this information.

Referring again to FIG. 1, in one embodiment sensor 102 may sense many biological states including, but not limited to, blood glucose level, blood oxygen level, and temperature. Sensor 102 may further include an exercise sensing device such as an accelerometer. In other embodiments, a separate blood glucose level sensor, blood oxygen level, temperature sensor and exercise sensing device may be used. Further embodiments may include sensors that detect various combinations of these and/or other biological states.

Reduction of Accumulated Insulin Formulation

An infusion pump for the delivery of an infusion formulation according to some embodiments has a fixed pump stroke volume, i.e., there is a certain minimum value of infusion formulation that must be accumulated before a pump stroke is executed, referred to in the present disclosure as a "pump stroke volume." Thus, if $I_{(t)}$ is calculated on a periodic basis, for example each minute, then the calculated amount for each minute may be some fractional part of a pump stroke volume. These fractional parts may be stored, for example, in a chamber or reservoir within or adjacent to the infusion pump until an amount equal to the pump stroke volume has been accumulated. At that time, a pump stroke may be executed and the insulin formulation delivered.

Figure 16A:
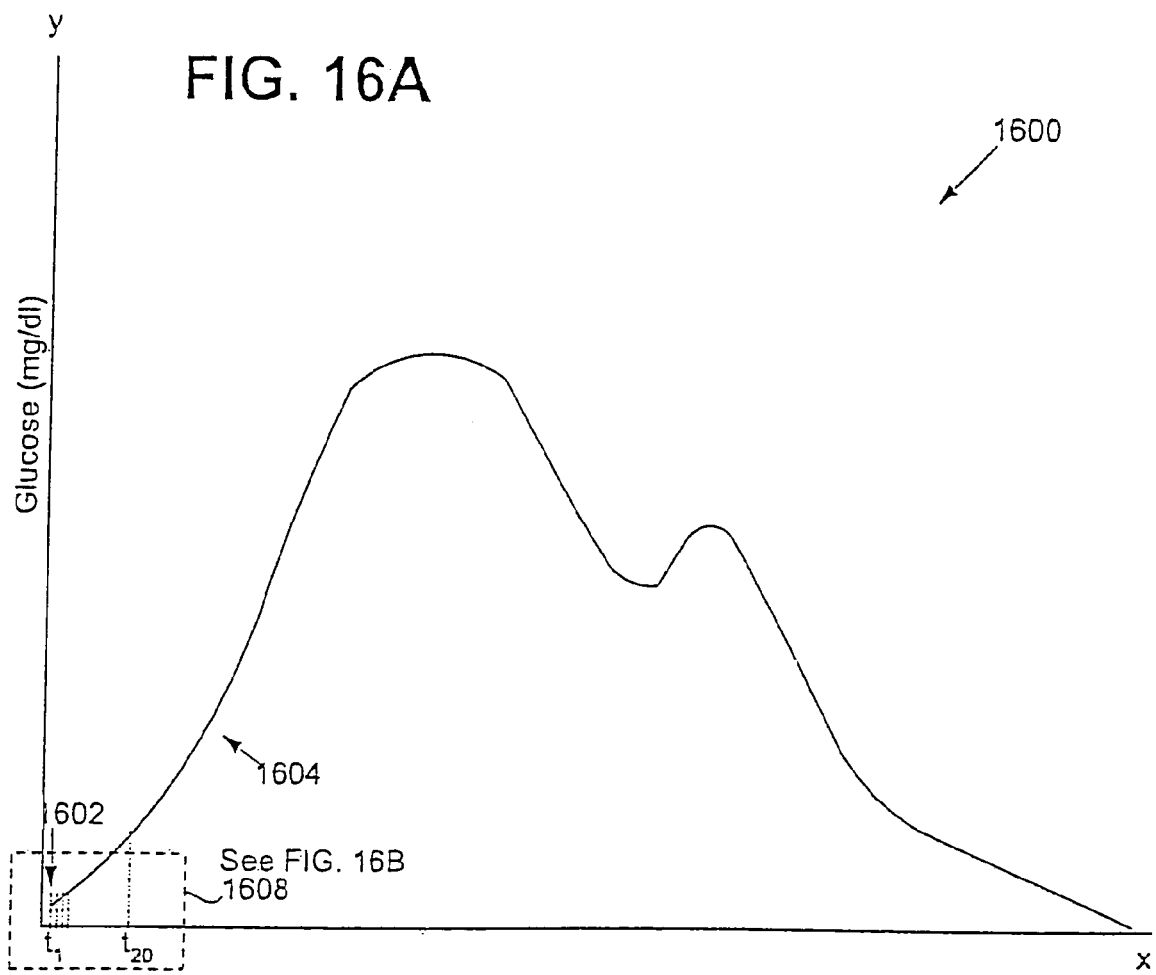
FIG. 16A shows a graph of a human blood glucose response for a user who has ingested a meal, illustrating a process whereby a pump stroke volume is accumulated, according to an embodiment of the invention.
Figure 16B:
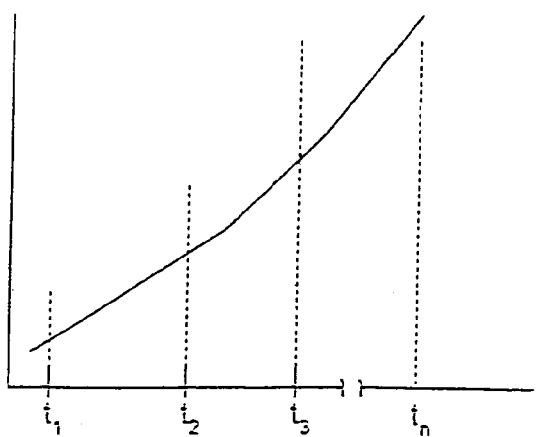
FIG. 16B shows a magnified view of a portion of the response curve of FIG. 16A.

The process where a pump stroke volume is accumulated is illustrated with reference to FIGS. 16A and 16B. FIG. 16A shows a graph of a human blood glucose response 1600 for a user who has ingested a meal at the point in time referred to by numeral 1602. FIG. 16B shows a magnified view of a portion of the response curve referred to in FIG. 15A by numeral 1608.

The blood glucose level begins to rise 1604. At time $t_1$, a first value for $I_{(t)}$ may be calculated using Equation 5. The amount of insulin formulation calculated as $I_{(t)}$ at time $t_1$ may be some fractional part of a pump stroke volume and may be stored in the accumulator. At time $t_2$, a second value for $I_{(t)}$ may be calculated. The amount of insulin formulation calculated as $I_{(t)}$ at time $t_2$ may also be some fractional part of a pump stroke volume and may be added to the first value stored in the accumulator. At time $t_3$, a third value for $I_{(t)}$ may be calculated, and so on.

At time $t_n$, an nth value of $I_{(t)}$ is calculated using Equation 5. The amount of insulin formulation calculated as $I_{(t)}$ at time $t_n$ is added to the accumulator, at which time the amount of insulin formulation in the accumulator is equivalent to a pump stroke volume. A pump stroke may now be executed to deliver the insulin formulation. Time $t_{(n)}$ may vary based on the pump stroke volume and the intervals at which $I_{(t)}$ is calculated.

As stated above, a process controller employing a closed-loop algorithm to control the delivery of an insulin formulation may be restricted to adding insulin formulation to the system, i.e., a body. Once insulin formulation is added to the system, normally the controller cannot retrieve it.

In further embodiments of the present invention, the accumulated volume of infusion formulation may be purged from the accumulation chamber or reservoir (also referred to in the present disclosure as the "accumulator") when the calculation of $I_{(t)}$ yields a result which shows that the blood glucose level is falling. Thus, although once delivered the infusion formulation may not be retrievable from the body, it may be retrieved from the accumulator before the pump stroke is executed.

In one embodiment, at any time before a pump stroke is executed, the controller may issue a command to purge the accumulator. For example, once it is determined that the blood glucose level is falling and delivery of further insulin formulation is not desirable, the amounts of insulin formulation that were calculated at times $t_1$ through $t_n$ while the blood glucose level was rising may be purged from the accumulator once the blood glucose level begins to fall. Thus, the accumulator may be advantageously "zeroed out." In addition, under circumstances involving high levels of blood glucose, the accumulator may be allowed to go negative, thus delaying the effect of future increases in blood glucose levels.

Programmable Control Parameters for Bolus Safety Limits

In further embodiments of the present invention, a large amount of insulin formulation (a "bolus") may be delivered by the infusion formulation delivery device, independently of Equation 5, when a user has a blood glucose level that is above a predefined value and is rising at or above a predefined rate, thus possibly indicating that a meal has been consumed. In other words, when the predefined criteria is met, the bolus amount may be delivered instead of a value of I(t) calculated using Equation 5.

In preferred embodiments, predefined bolus safety limits are included as control parameters for the closed-loop algorithm. In some embodiments, the bolus control parameters may be programmable in real time. Table 2 shows example bolus safety limit control parameters that may be programmable in different embodiments of the present invention. In some embodiments, all the control parameters shown in Table 2 are programmable. In one embodiment, the control parameters shown in Table 2 may be programmed in real time. Table 2 also includes example values for each control parameter.

TABLE 2

| Control Parameter | Value |
| --- | --- |
| Bolus amount | Up to 25 units in increments of 0.2 units; preferably 1-8 units |
| Time between boluses | One minute to 24 hours; preferably 30-60 minutes |
| Bolus threshold | 50-200 mg/dl; preferably 80-160 mg/dl |
| Bolus trend | Varies from individual to individual; typically 1-5 mg/dl/min for humans; preferably 2-4 mg/dl/min |

Figure 17:
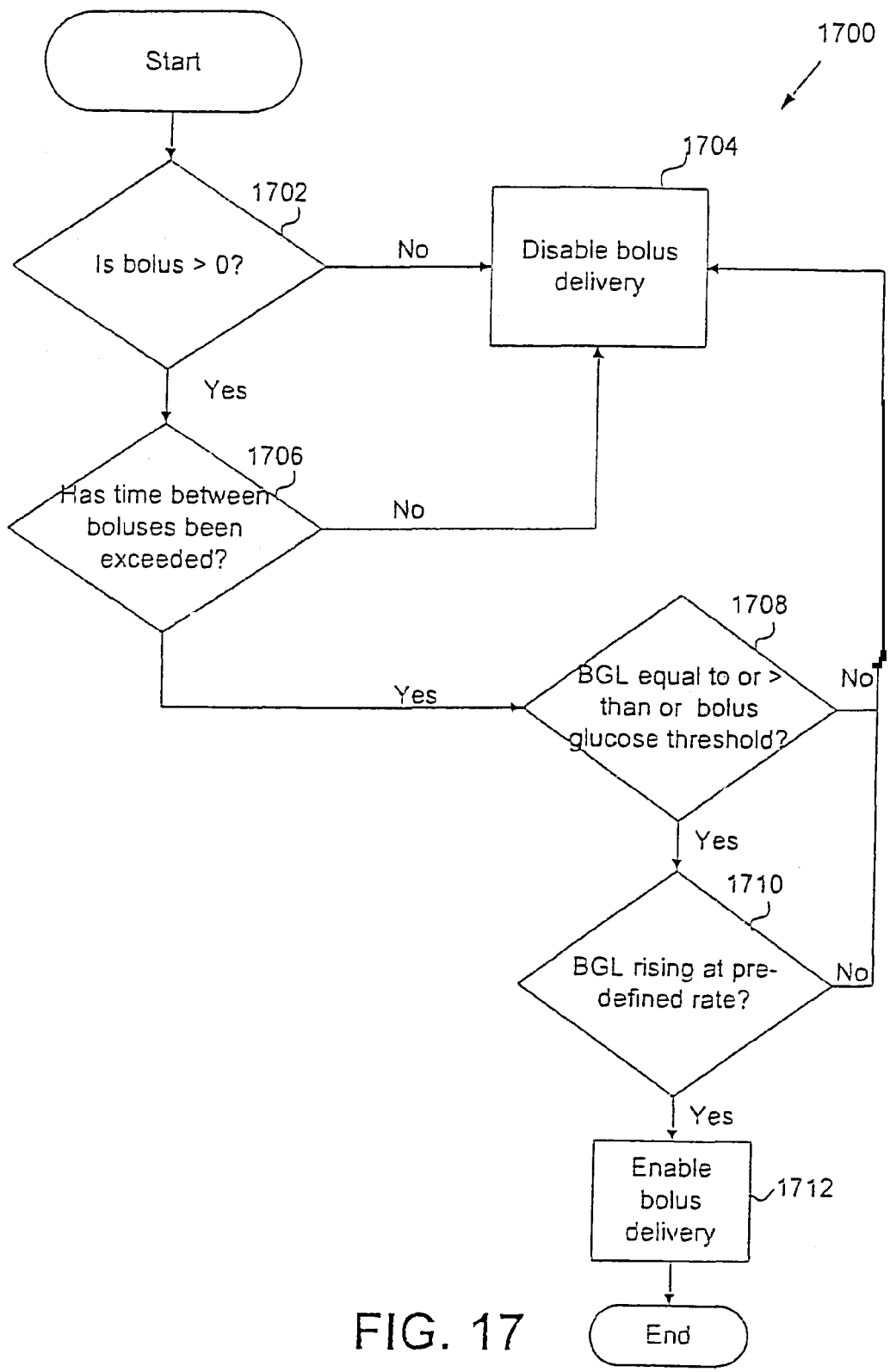
FIG. 17 shows a flow diagram illustrating a verification of the status of each bolus control parameter before a bolus delivery is executed, according to an embodiment of the invention.

Preferred embodiments of the present invention use the programmable control parameters shown in Table 2 to advantageously provide safety limits to be used in order to reduce the possibility of erroneously delivering a bolus by ensuring that the status of each control parameter is verified before a bolus delivery is executed by the infusion formulation delivery device. This is illustrated by flow diagram 17, shown in FIG. 17.

As discussed above, the blood glucose level is sampled at intervals, for example every minute. In some embodiments, each time the blood glucose level is sampled, a check is performed by the closed-loop algorithm to determine the status of the control parameters shown in Table 2.

In one embodiment, the closed-loop algorithm first determines if a bolus delivery feature is enabled 1702. This may be determined, for example, by comparing a predefined "bolus amount" control parameter value with zero. If the value is equal to zero, bolus delivery may be disabled 1704. If the value is greater than zero, the "time between boluses" control parameter may be checked 1706.

The "time between boluses" control parameter determines whether or not a predefined time interval has been exceeded since the last bolus delivery. If the time interval between bolus deliveries has not been exceeded, bolus delivery may be disabled 1704. If the time interval between bolus deliveries has been exceeded, the "glucose threshold" control parameter may be checked 1708.

The "glucose threshold" control parameter determines whether or not a predefined blood glucose level has been reached. If the predefined blood glucose level has not been reached, the bolus delivery feature may be disabled 1704. If the predefined blood glucose level has been reached, then the "bolus trend" control parameter may be checked 1710.

The "bolus trend" control parameter determines whether or not the blood glucose level is rising at a predefined rate. If the blood glucose level is not rising at the predefined rate, then the bolus delivery feature may be disabled 1704. If the blood glucose level is rising at the predefined rate, then the bolus delivery feature may be enabled 1712. Also, according to an embodiment of the present invention, additional signal processing may be implemented to detect a signature of a meal, which may then be used to enable the bolus feature.

Thus, embodiments advantageously provide bolus safety limits to reduce the possibility of erroneously delivering a bolus by ensuring that predefined conditions for delivery of a bolus are met by testing predefined control parameters that are programmable. Thus, the closed-loop algorithm reduces the possibility of delivering too much insulin formulation as a bolus and thus reduces the risks of hypoglycemia to the user.

Programmable Control Parameters for Maximum Insulin Formulation Delivery Amounts In yet other embodiments of the present invention, additional safety limits may be used to ensure that no more than a predefined maximum amount of insulin formulation is stored in the accumulator at each sampling interval. For example, when the sampling interval is one minute, a limit may be set on the maximum amount of insulin formulation that may be stored in the accumulator each minute. This amount may be programmable.

Similarly, in yet a further embodiment, a limit may be set on the maximum amount of insulin formulation that may be delivered by the infusion formulation delivery device in one hour. This amount may also be programmable.

Thus, by "clamping" the maximum amount that may be stored in the accumulator at each sampling period and the maximum amount that may be delivered to the body each hour, embodiments of the present invention reduce the possibility of delivering too much insulin formulation and thus reduce the risks of hypoglycemia to the user.

Accordingly, a number of aspects and features of preferred embodiments of the closed-loop algorithm described above may provide programmable control parameters for tuning the closed-loop algorithm to more accurately determine an amount of insulin formulation to be delivered in response to a sensed blood glucose level in order to reduce the risks of hypoglycemia to a user. Additional aspects and features of preferred embodiments of the closed-loop algorithm may provide safety limits which reduce the risks of hypoglycemia to a user. The aspects and features described above may be combined to provide maximum control and safety for a user. However, the foregoing description of embodiments of the invention has been presented for the purposes of illustration and description. It is not intended to be exhaustive or to limit the invention to the precise forms disclosed. Many modifications and variations are possible in light of the above teaching.

For example, several embodiments of the closed-loop algorithm were described above in relation to a graph of a human blood glucose response for a user who has ingested a meal. These examples are meant to be illustrative and not limiting. The meal event is used as an example of an event which may lead to changes in insulin production by the pancreas of a non-diabetic person, and for which the tuning of the closed-loop algorithm using control parameters may be advantageous. However, the meal event should not be considered to be a limitation on the events which may affect glucose levels in the human body, and thus on the events for which adjustable control parameters for tuning the closed-loop algorithm may be advantageous.

Thus, the programmable control parameters may be adjusted to adjust the closed-loop algorithm to more accurately calculate the amount of insulin formulation to be delivered during or after other events which may affect the blood glucose response of a user. For example, The programmable control parameters may be adjusted to more accurately calculate the amount of insulin formulation to be delivered during or after exercise events, medication events, stress events, sleep events, and the like.

Having disclosed exemplary embodiments and the best mode, modifications and variations may be made to the disclosed embodiments while remaining within the scope of the invention as defined by the following claims.

What is claimed is:

1. A method for delivering insulin formulation, the method comprising:
    delivering an amount of insulin formulation in accordance with a predefined delivery profile having a plurality of components, including a basal component that comprises a predefined amount of insulin formulation that is delivered to maintain a target blood glucose level;
    sampling a blood glucose level at predefined timed intervals;
    comparing the sampled blood glucose level to a predefined blood glucose level threshold; and
    disabling delivery of the basal component of the delivery profile, if the sampled blood glucose level is less than the predefined blood glucose level threshold.

2. The method recited in claim 1, further comprising:
    determining if a predefined time interval has been exceeded since a previous bolus delivery; and
    disabling the bolus delivery if the predefined time interval has not been exceeded.

3. The method of claim 1, wherein comparing the sampled blood glucose level to the predefined blood glucose level threshold is performed independent of values other than the sampled blood glucose level and the predefined blood glucose level threshold.

4. The method recited in claim 1, wherein the basal rate component comprises an amount of insulin to deliver when the blood glucose level is at a desired level, to maintain the blood glucose level at the desired level.

5. The method recited in claim 1, wherein the plurality of components further includes a difference component based on the difference between a desired blood glucose level and the sampled blood glucose level.

6. The method recited in claim 1, wherein the plurality of components further includes a derivative component based on the rate at which the blood glucose level is changing.

7. The method recited in claim 1, wherein the plurality of components further includes a derivative component based on the rate at which the blood glucose level is changing and also based on whether or not the blood glucose level is rising.

8. The method recited in claim 1, wherein delivering an insulin formulation comprises defining a delivery amount at a time (t) using the predefined delivery profile, including determining the plurality of components for the time (t) and adding the plurality of components determined for the time (t).

9. A method for delivering an insulin formulation, the method comprising:
    delivering an amount of insulin formulation in accordance with a predefined delivery profile having a plurality of components, including a basal component;
    sampling a blood glucose level at predefined timed intervals;
    comparing the sampled blood glucose level to a predefined blood glucose level threshold; and
    disabling delivery of the basal component of the delivery profile, if the sampled blood glucose level crosses the predefined blood glucose level threshold.

10. The method recited in claim 9, wherein disabling delivery of the basal component of the delivery profile occurs if the sampled blood glucose level is less than the predefined blood glucose level threshold.

11. The method recited in claim 9, wherein the insulin formulation is delivered as a bolus.

12. The method recited in claim 11, further comprising:
    determining if a predefined time interval has been exceeded since a previous bolus delivery; and
    disabling the bolus delivery if the predefined time interval has not been exceeded.

13. The method recited in claim 11, further comprising:
    determining a time window for disabling a calculation of a delivery rate of the insulin formulation;
    sampling a current time;
    determining if the current time is within the time window; and
    disabling the calculation of the delivery rate of the insulin formulation if the current time is within the time window.

14. The method recited in claim 13, wherein determining a time window further comprises providing programmable start and stop times for the time window.

15. The method recited in claim 14, wherein the programmable start and stop times for the time window are determined from historical physiological data.

16. The method recited in claim 13, further comprising enabling the calculation of the delivery rate of the insulin formulation if the current time is not within the time window.

17. The method recited in claim 13, further comprising delivering a minimal insulin formulation if the current time is within the time window.

18. The method recited in claim 13, further comprising delivering no insulin formulation if the current time is within the time window.

19. The method recited in claim 9, further comprising delivering a bolus of insulin formulation if the sampled blood glucose level is greater than the predefined blood glucose level threshold.

20. The method recited in claim 9, further comprising:
calculating an amount by which the sampled blood glucose level exceeds the predefined blood glucose level threshold;
determining a rate at which the sampled blood glucose level is changing; and
delivering an amount of insulin formulation based on the amount which the sampled blood glucose level exceeds the predefined blood glucose level threshold and the rate at which the sampled blood glucose level is changing.

21. The method recited in claim 20, further comprising introducing an adjustment into the amount of insulin formulation delivered, wherein the adjustment is not related to the amount which the sampled blood glucose level exceeds the predefined blood glucose level threshold or the rate at which the sampled blood glucose level is changing.

22. The method recited in claim 21, wherein the adjustment is introduced via programmable control parameters.

23. The method recited in claim 20, wherein determining a rate at which the sampled blood glucose level is changing occurs at predetermined intervals.

24. The method recited in claim 23, wherein the predetermined intervals are programmable.

25. The method recited in claim 20, wherein delivering an an amount of insulin formulation comprises delivering a basal rate of insulin formulation.

26. The method recited in claim 20, further comprising calculating an amount by which the sampled blood glucose level is offset over time from the predefined blood glucose level threshold.

27. The method recited in claim 8, further comprising filtering out high frequency components of the sampled blood glucose level.

28. The method recited in claim 27, wherein filtering comprises filtering with a low pass filter.

29. A system for delivering an insulin formulation comprising:
an infusion device for delivering an amount of insulin formulation in accordance with control commands based on a predefined delivery profile having a plurality of components, including a basal rate component;
a data acquisition unit for sampling a blood glucose level at predefined timed intervals;
a comparator for comparing the sampled blood glucose level acquired by the data acquisition unit to a predefined blood glucose level threshold; and
a controller configured to provide control commands to the infusion device including a command for disabling delivery of the basal component of the delivery profile, if the sampled blood glucose level crosses the predefined blood glucose level threshold.

30. The system of claim 29, wherein the controller is configured to disable insulin formulation delivery if the sampled blood glucose level is less than the predefined blood glucose level threshold.

31. The system of claim 29, wherein the controller is configured to cause the insulin formulation to be delivered as a bolus.

32. The system of claim 31, wherein the data acquisition unit is further configured to determine if a predefined time interval has been exceeded since a previous bolus delivery; and
wherein the controller disables the bolus delivery if the predefined time interval has not been exceeded.

33. The system of claim 31, wherein the data acquisition unit is further configured to determine if the sampled blood glucose level is rising at a predefined rate; and
wherein the controller disables the bolus delivery if the sampled blood glucose level is rising at a rate less than the predefined rate.

34. The system of claim 31, wherein the data acquisition unit is configured to sample a current time; and
wherein the controller is configured to:
determine a time window for disabling a calculation of a delivery rate of the insulin formulation;
determine if the current time is within the time window; and
disable the calculation of the delivery rate of the insulin formulation if the current time is within the time window.

35. The system of claim 34, wherein the controller is configured to provide programmable start and stop times for the time window.

36. The system of claim 35, wherein the controller determines the programmable start and stop times for the time window from historical physiological data.

37. The system of claim 34, wherein the controller is configured to enable the calculation of the delivery rate of the insulin formulation if the current time is not within the time window.

38. The system of claim 34, wherein the controller is configured to cause delivery of a minimal insulin formulation if the current time is within the time window.

39. The system of claim 34, wherein the controller is configured to cause delivery of no insulin formulation if the current time is within the time window.

40. The system of claim 29, wherein the controller causes an insulin formulation to be delivered if the sampled blood glucose level is greater than the predefined blood glucose level threshold.

41. The system of claim 29, wherein the controller is further configured to:
calculate an amount by which the sampled blood glucose level exceeds the predefined blood glucose level threshold;
determine a rate at which the sampled blood glucose level is changing; and
deliver an amount insulin formulation based on the amount which the sampled blood glucose level exceeds the predefined blood glucose level threshold and the rate at which the sampled blood glucose level is changing.

42. The system of claim 41, wherein the controller is configured to cause an adjustment to be introduced into the amount of insulin formulation delivered not related to the amount which the sampled blood glucose level exceeds the predefined blood glucose level threshold or the rate at which the sampled blood glucose level is changing.

43. The system of claim 42, wherein the controller is configured with programmable control parameters for introduction of the adjustment.

44. The system of claim 41, wherein the controller is configured to determine at predetermined intervals the rate at which the sampled blood glucose level is changing.

45. The system of claim 44, wherein the predetermined intervals are programmable.

46. The system of claim 41, wherein the controller is configured to calculate an amount by which the sampled blood glucose level is offset over time from the predefined blood glucose level threshold.

47. The system of claim 29, further comprising a filter for filtering out high frequency components of the sampled blood glucose level.

48. The system of claim 47, wherein the filter is a low pass filter.

* * * * *